(12) United States Patent
El Qacemi et al.

(10) Patent No.: US 11,001,577 B2
(45) Date of Patent: *May 11, 2021

(54) PESTICIDALLY ACTIVE AZETIDINE SULFONES AMIDE ISOXAZOLINE DERIVATIVES

(71) Applicant: SYNGENTA PARTICIPATIONS AG, Basel (CH)

(72) Inventors: Myriem El Qacemi, Stein (CH); Jérôme Yves Cassayre, Münchwilen (CH); Thomas Pitterna, Stein (CH); André Stoller, Stein (CH); Peter Renold, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/471,497

(22) PCT Filed: Dec. 18, 2017

(86) PCT No.: PCT/EP2017/083297
§ 371 (c)(1),
(2) Date: Jun. 19, 2019

(87) PCT Pub. No.: WO2018/114791
PCT Pub. Date: Jun. 28, 2018

(65) Prior Publication Data
US 2020/0123143 A1    Apr. 23, 2020

(30) Foreign Application Priority Data
Dec. 19, 2016    (EP) ..................................... 16205192

(51) Int. Cl.
*C07D 413/12* (2006.01)
*A01N 43/80* (2006.01)

(52) U.S. Cl.
CPC ........... *C07D 413/12* (2013.01); *A01N 43/80* (2013.01)

(58) Field of Classification Search
None
See application file for complete search history.

(56) References Cited

FOREIGN PATENT DOCUMENTS

| WO | 2009080250 A2 | 7/2009 |
| WO | 2013026931 A1 | 2/2013 |
| WO | 2015113927 A1 | 8/2015 |

OTHER PUBLICATIONS

Extended European Search Report dated Mar. 20, 2017 for EP Application No. 16205192.4.
PubChem Compound NCBI; CID 121685651.
PubChem Compound NCBI; CID 66184768.
PubChem Compound NCBI; CID 66185361.
Chemical Abstracts Service, USA; Abstract Accession No. 1604597-98-9.
Extended European Search Report for EP Application No. 16205192.4 dated Mar. 20, 2017.
NIH, U.S. National Library of Medicine, PubChem Open Chemistry Database Compound National Center for Biotechnology Information, CID 121685651, created Sep. 22, 2016.
NIH, U.S. National Library of Medicine, PubChem Open Chemistry Database Compound National Center for Biotechnology Information, CID 66184768, created Oct. 24, 2012.
NIH, U.S. National Library of Medicine, PubChem Open Chemistry Database Compound National Center for Biotechnology Information, CID 66185361, created Oct. 24, 2012.
Chemical Abstracts Service, USA; Abstract Accession No. 1604991-06-1 dated May 14, 2014.
Chemical Abstracts Service, USA; Abstract Accession No. 1604597-98-9 dated May 14, 2014.

*Primary Examiner* — Alton N Pryor
(74) *Attorney, Agent, or Firm* — Baker & Hostetler LLP; Toni-Junell Herbert

(57) ABSTRACT

Compounds of formula (I) wherein the substituents are as defined in claim 1, and the agrochemically acceptable salts, stereoisomers, enantiomers, tautomers and N-oxides of those compounds, can be used as insecticides and can be prepared in a manner known per se.

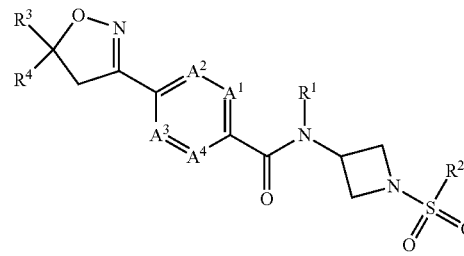

21 Claims, No Drawings

PESTICIDALLY ACTIVE AZETIDINE SULFONES AMIDE ISOXAZOLINE DERIVATIVES

CROSS-REFERENCE TO RELATED APPLICATIONS

This application is a 371 National Stage application of International Application No. PCT/EP2017/083297, filed Dec. 18, 2017, which claims priority to EP 16205192.4 filed Dec. 19, 2016, the entire contents of which applicationa are hereby incorporated by reference.

The present invention relates to pesticidally active, in particular insecticidally active azetidine sulfones amide isoxazolines, to compositions comprising those compounds, and to their use for controlling animal pests (including arthropods and in particular insects or representatives of the order Acarina).

Certain isoxazoline derivatives with insecticidal properties are disclosed, for example, in WO2011067272.

There have now been found novel pesticidally active azetidine sulfones amide isoxazoline derivatives.

The present invention accordingly relates to compounds of formula (I)

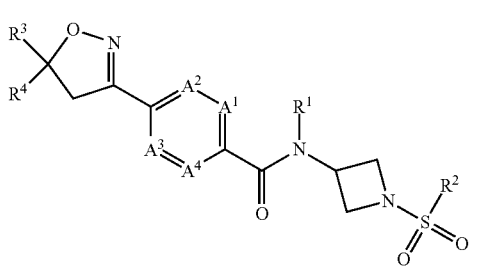

wherein $A^1$, $A^2$, $A^3$ and $A^4$, independently of one another, are C—H, C—$R^5$ or nitrogen;

$R^1$ is hydrogen, $C_1$-$C_6$alkyl, $C_1$-$C_6$alkylcarbonyl-, $C_1$-$C_6$alkoxy, $C_1$-$C_8$alkoxy-$C_1$-$C_8$alkyl or $C_1$-$C_8$alkoxycarbonyl;

$R^2$ is halogen, $C_1$-$C_8$alkoxy, amino, $C_2$-$C_6$alkenyl, $C_2$-$C_6$alkynyl, $C_1$-$C_8$haloalkoxy, $C_1$-$C_8$alkylamino, $C_1$-$C_8$alkylamino wherein the alkyl group is substituted by $R^{6a}$, $C_1$-$C_8$alkenylamino, —NHC(O)$NR^aR^b$, $C_1$-$C_8$dialkylamino, $C_1$-$C_8$dialkylamino wherein one or both of the alkyl groups are independently substituted by $R^{6a}$, $C_1$-$C_8$dialkenylamino, $C_1$-$C_8$haloalkylamino, $C_1$-$C_8$dihaloalkylamino, $C_3$-$C_8$cycloalkyl, $C_1$-$C_8$alkyl substituted by $R^{6a}$, $C_2$-$C_6$alkenyl substituted by $R^{6b}$, $C_2$-$C_6$alkynyl substituted by $R^{6b}$, $C_3$-$C_8$cycloalkyl substituted by $R^{6b}$ or —$R^cCO(O)R^d$, wherein $R^a$, $R^b$, $R^c$ and $R^d$ are independently of each other $C_1$-$C_8$alkyl;

$R^3$ is $C_1$-$C_8$haloalkyl;

$R^4$ is aryl, aryl substituted by one to three $R^7$, heteroaryl or heteroaryl substituted by one to three $R^7$;

each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —$CH_2$—$CH_2$—$CH_2$— bridge, a —CH=CH—CH=CH— bridge or a —N=CH—CH=CH— bridge;

each $R^{6a}$ is independently cyano, $C_3$-$C_8$cycloalkyl, $C_2$-$C_8$alkynyl, $C_1$-$C_8$alkoxy, $C_1$-$C_8$alkoxy-$C_1$-$C_8$alkoxy, $C_1$-$C_8$haloalkoxy, $C_1$-$C_8$alkylcarbonyloxy, —C(O)$NH_2$ or =$NOR^f$, wherein $R^f$ is $C_1$-$C_8$ alkyl;

each $R^{6b}$ is independently halogen, cyano, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy or $C_1$-$C_8$alkoxy$C_1$-$C_8$alkyl; and each $R^7$ is independently halogen, cyano, nitro, $C_1$-$C_8$alkyl, $C_1$-$C_8$haloalkyl, $C_1$-$C_8$alkoxy or $C_1$-$C_8$haloalkoxy;

and agrochemically acceptable salts, stereoisomers, enantiomers, tautomers and N-oxides of those compounds.

Compounds of formula (I) which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

Where substituents are indicated as being substituted, this means that they carry one or more identical or different substituents, e.g. one to three substituents. Where a group is indicated as being substituted, e.g. alkyl, this includes those groups that are part of other groups, e.g. the alkyl in alkoxy or phenyl in phenyloxy. The number of substituents does not exceed the number of available C—H and N—H bonds.

The alkyl groups occurring in the definitions of the substituents can be straight-chain or branched and are, but are not limited to, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, but is not limited to, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, but is not limited to, methoxy, ethoxy, propoxy, i-propoxy, n-butoxy, isobutoxy, sec-butoxy and tert-butoxy and also the isomeric pentyloxy and hexyloxy radicals.

Alkoxyalkyl is, but are not limited to, methoxymethyl, methoxyethyl, ethoxymethyl, ethoxyethyl, n-propoxymethyl, n-propoxyethyl, isopropoxymethyl or isopropoxyethyl.

Alkoxycarbonyl is, but are not limited to, methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms and are, for example, cyclopropyl, cyclobutyl, cyclopentyl and cyclohexyl.

As used herein, the term "$C_2$-$C_8$alkynyl" refers to a straight or branched hydrocarbon chain radical group consisting solely of carbon and hydrogen atoms, containing at least one triple bond, having from two to eight carbon atoms, and which is attached to the rest of the molecule by a single bond. Examples of $C_2$-$C_8$ alkynyl include, but are not limited to, ethynyl, prop-1-ynyl, but-1-ynyl and but-2-ynyl.

As used herein, the term "$C_2$-$C_8$alkenyl" refers to a straight or branched hydrocarbon chain radical group consisting solely of carbon and hydrogen atoms, containing at least one double bond, having from two to eight carbon atoms, and which is attached to the rest of the molecule by a single bond.

Examples of $C_2$-$C_8$alkenyl include, but are not limited to, prop-1-enyl, but-1-enyl and but-2-enyl.

Aryl means a six to fourteen membered aromatic carbocyclic ring system which can be mono-, bi- or tricyclic. Examples of such rings include phenyl, indenyl, naphthalenyl, anthranyl, or phenanthrenyl. A preferred aryl group is phenyl.

Heteroaryl stands for a five to six membered aromatic ring system comprising 1 to 3 hetero atoms selected from the group consisting of nitrogen, oxygen and sulfur, it not being possible for the ring system to contain more than 2 oxygen atoms and more than 2 sulfur atoms. Examples of heteroaryl are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl. A preferred aryl group is pyridyl.

The compounds of formula (I) according to the invention also include hydrates which may be formed during the salt formation.

Preferably the present invention accordingly relates to compounds of formula (I)

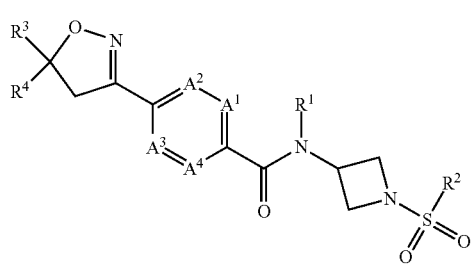

(I)

wherein $A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl;

$R^2$ is halogen, amino, $C_1$-$C_8$alkoxy, $C_2$-$C_6$alkenyl, $C_2$-$C_6$alkynyl, $C_1$-$C_8$haloalkoxy, $C_1$-$C_8$alkylamino, $C_1$-$C_8$alkylamino wherein the alkyl group is substituted by $R^{6a}$, $C_1$-$C_8$alkenylamino, —NHC(O)NR$^a$R$^b$, $C_1$-$C_8$dialkylamino, $C_1$-$C_8$dialkylamino wherein one or both of the alkyl groups are independently substituted by $R^{6a}$, $C_1$-$C_8$dialkylamino, $C_1$-$C_8$haloalkylamino, $C_1$-$C_8$dihaloalkylamino, $C_3$-$C_8$cycloalkyl, $C_1$-$C_8$alkyl substituted by $R^{6a}$, $C_2$-$C_6$alkenyl substituted by $R^{6b}$, $C_2$-$C_6$alkynyl substituted by $R^{6b}$, $C_3$-$C_8$cycloalkyl substituted by $R^{6b}$ or —R$^c$CO(O)R$^d$, wherein R$^a$, R$^b$, R$^c$ and R$^d$ are independently of each other $C_1$-$C_8$ alkyl;

$R^3$ is $C_1$-$C_8$haloalkyl;

$R^4$ is six to fourteen membered aryl, six to fourteen membered aryl substituted by one to three $R^7$, or five to six membered heteroaryl which can be optionally substituted by one or more $R^5$ and which comprises 1 to 3 heteroatoms selected from the group consisting of nitrogen, oxygen and sulfur, it not being possible for the ring system to contain more than 2 oxygen atoms or more than 2 sulfur atoms; each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy or $C_1$-$C_8$alkoxycarbonyl-, or two $R^5$ on adjacent carbon atoms together form a —$CH_2$—$CH_2$—$CH_2$— bridge, a —CH=CH—CH=CH— bridge or a —N=CH—CH=CH— bridge;

each $R^{6a}$ is independently cyano, $C_3$-$C_8$cycloalkyl, $C_2$-$C_8$alkynyl, $C_1$-$C_8$alkoxy, $C_1$-$C_8$alkoxy-$C_1$-$C_8$alkoxy, $C_1$-$C_8$haloalkoxy, $C_1$-$C_8$alkylcarbonyloxy, —C(O)NH$_2$ or =NOR$^f$, wherein R$^f$ is $C_1$-$C_8$ alkyl;

each $R^{6b}$ is independently halogen, cyano, $C_1$-$C_4$alkyl, $C_3$-$C_6$cycloalkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_1$-$C_4$alkoxy, $C_1$-$C_4$haloalkoxy or $C_1$-$C_4$alkoxy$C_1$-$C_4$alkyl; and each $R^7$ is independently halogen, cyano, nitro, $C_1$-$C_8$alkyl, $C_1$-$C_8$haloalkyl, $C_1$-$C_8$alkoxy or $C_1$-$C_8$haloalkoxy;

and agrochemically acceptable salts, stereoisomers, enantiomers, tautomers and N-oxides of those compounds.

Preferably at least two of $A^1$, $A^2$, $A^3$ and $A^4$ are different from nitrogen.

Preferably $A^1$ is C—H or C—$R^5$; more preferably $A^1$ is C—$R^5$.

Preferably $A^2$ is C—H or C—$R^5$; more preferably $A^2$ is C—H.

Preferably $A^3$ is C—H or N; more preferably $A^3$ is C—H.

Preferably $A^4$ is C—H or N; more preferably $A^4$ is C—H.

More preferably $A^1$ is C—$R^5$, and $A^2$, $A^3$ and $A^4$ are C—H.

Embodiment E1

In a preferred embodiment of the invention, $R^1$ is hydrogen, $C_1$-$C_8$alkyl, $C_1$-$C_8$alkylcarbonyl- or $C_1$-$C_8$alkoxycarbonyl; more preferably $R^1$ is hydrogen, methyl, ethyl, methylcarbonyl-, ethylcarbonyl-, t-butylcarbonyl-, isopropycarbonyl-, ethoxycarbonyl or methoxycarbonyl; more preferably $R^1$ is hydrogen, methyl, ethyl, methylcarbonyl-, or methoxycarbonyl; more preferably $R^1$ is hydrogen, methyl or ethyl; more preferably $R^1$ is hydrogen, methylcarbonyl-, or methoxycarbonyl; especially $R^1$ is hydrogen or methyl; more especially $R^1$ is hydrogen or methoxycarbonyl; most especially $R^1$ is hydrogen.

Embodiment E2

In a preferred embodiment of the invention,
preferably $R^2$ is halogen, amino, $C_1$-$C_4$alkoxy, $C_2$-$C_4$alkenyl, $C_2$-$C_4$alkynyl, $C_1$-$C_4$haloalkoxy, $C_1$-$C_4$alkylamino, $C_1$-$C_4$alkylamino wherein the alkyl group is substituted by $R^{6a}$, $C_1$-$C_4$alkenylamino, —NHC(O)NR$^a$R$^b$, $C_1$-$C_4$dialkylamino, $C_1$-$C_4$dialkylamino wherein one or both of the alkyl groups are independently substituted by $R^{6a}$, $C_1$-$C_4$dialkenylamino, $C_1$-$C_4$haloalkylamino, $C_1$-$C_4$dihaloalkylamino, $C_3$-$C_6$cycloalkyl, $C_1$-$C_4$alkyl substituted by $R^{6a}$, $C_2$-$C_4$alkenyl substituted by $R^{6b}$, $C_2$-$C_4$alkynyl substituted by $R^{6b}$, $C_3$-$C_6$cycloalkyl substituted by $R^{6b}$ or —R$^c$CO(O)R$^d$, wherein R$^a$, R$^b$, R$^c$ and R$^d$ are, independently, $C_1$-$C_8$ alkyl; more preferably $R^2$ is halogen, amino, $C_2$-$C_4$alkenyl, $C_1$-$C_4$haloalkoxy, $C_1$-$C_4$alkylamino, $C_1$-$C_4$dialkylamino, $C_1$-$C_4$haloalkylamino, $C_1$-$C_4$dihaloalkylamino, $C_3$-$C_6$cycloalkyl, $C_1$-$C_4$alkyl substituted by $R^{6a}$, or $C_3$-$C_6$cycloalkyl substituted by $R^{6b}$; especially $R^2$ is halogen, amino, cyclopropyl, vinyl, dimethylamino, bis-2,2,2-trifluoroethylamino, bis-2,2-difluoroethylamino, methylamino, 2,2,2-trifluoroethylamino, 2,2-difluoroethylamino, amino, acetonitrile, 1-methoxymethylcyclopropan-1-yl or 2,2,2-trifluoroethoxy; more especially $R^2$ is fluorine, cyclopropyl, 1-cyanocyclopropyl, 1-methylcyclopropyl, cyclobutyl, dimethylamino, methylamino, ethylamino, isopropylamino, propylamino, isopropylmethylamino, cyclobutylmethylamino, cyclopropylmethylamino, bis-allylamino, bis-cyclopropylmethylamino, 2-methylpropanenitrile, bis-2,2,2-trifluoroethylamino, bis-2,2-difluoroethylamino methylamino, 2,2,2-trifluoroethylamino, 2,2-difluoroethylamino, 2,2,2-trifluoroethoxy, amino, methyl propanoate, methyl 2,2-dimethylpropanoate or acetonitrile.

Embodiment E3

In a preferred embodiment of the invention,
preferably $R^3$ is $C_1$-$C_4$haloalkyl; more preferably $R^3$ is chlorodifluoromethyl or trifluoromethyl; most preferably $R^3$ is trifluoromethyl.

Embodiment E4

In a preferred embodiment of the invention,
preferably $R^4$ is six to fourteen membered aryl, six to fourteen membered aryl substituted by one to three $R^7$ or five to six membered heteroaryl which can be optionally substituted by one or more $R^7$ and which comprises 1 to 3 heteroatoms selected from the group consisting of nitrogen, oxygen and sulfur, it not being possible for the ring system to contain more than 2 oxygen atoms or more than 2 sulfur atoms; more preferably $R^4$ is six to fourteen membered aryl or six to fourteen membered aryl substituted by one to three $R^7$; most preferably $R^4$ is phenyl or phenyl substituted by one to three $R^7$;
even more preferably $R^4$ is phenyl substituted by one to three $R^7$; especially $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl or 3,4,5-trichloro-phenyl.

Embodiment E5

In a preferred embodiment of the invention,
preferably each $R^5$ is independently halogen, cyano, nitro, $C_1$-$C_8$alkyl, $C_3$-$C_8$cycloalkyl, $C_1$-$C_8$haloalkyl, or $C_2$-$C_8$alkenyl, or two $R^5$ on adjacent carbon atoms together form a —$CH_2$—$CH_2$—$CH_2$— bridge or a —CH=CH—CH=CH— bridge; more preferably each $R^5$ is independently halogen, cyano, nitro, $C_1$-$C_8$alkyl, $C_2$-$C_8$ alkenyl, $C_3$-$C_8$cycloalkyl, $C_1$-$C_8$haloalkyl, or two $R^5$ on adjacent carbon atoms together form a —$CH_2$—$CH_2$—$CH_2$— bridge or a —CH=CH—CH=CH— bridge; even more preferably each $R^5$ is independently bromo, chloro, fluoro, cyano, nitro, methyl, ethyl, trifluoromethyl, cyclopropyl, vinyl, or two $R^5$ on adjacent carbon atoms together form a —$CH_2$—$CH_2$—$CH_2$— bridge or a —CH=CH—CH=CH— bridge; yet even more preferably each $R^5$ is independently bromo, chloro, ethyl, cyclopropyl, trifluoromethyl, vinyl, methyl, or two $R^5$ on adjacent carbon atoms together form a —$CH_2$—$CH_2$—$CH_2$— bridge or a —CH=CH—CH=CH— bridge; more preferably each $R^5$ is independently chloro, bromo, trifluoromethyl, ethyl, methyl, or two $R^5$ on adjacent carbon atoms together form a —$CH_2$—$CH_2$—$CH_2$— bridge, most preferably each $R^5$ is independently methyl or two $R^5$ on adjacent carbon atoms together form a —$CH_2$—$CH_2$—$CH_2$— bridge.

Embodiment E6

In a preferred embodiment of the invention,
preferably each $R^7$ is independently halogen, cyano, $C_1$-$C_4$alkyl, $C_1$-$C_4$haloalkyl, $C_1$-$C_4$alkoxy or $C_1$-$C_4$haloalkoxy; more preferably each $R^7$ is independently methyl, fluoro, chloro, bromo, trifluoromethyl, trifluoromethoxy, cyano or methoxy, even more preferably each $R^7$ is independently Cl, Br, F or $CF_3$;

Each of the Embodiments E1 to E6 can be combined to a new preferred group of compounds of formula (I) as shown in the following Table E.

TABLE E

| preferred embodiments of the formula (I): | | | | |
|---|---|---|---|---|
| Combination | Combination | Combination | Combination | Combination |
| E1 + E2 | E1 + E6 | E3 + E4 + E5 | E2 + E5 + E6 | E2 + E3 + E4 + E6 |
| E1 + E3 | E2 + E6 | E1 + E2 + E4 | E3 + E4 + E6 | E2 + E4 + E5 + E6 |
| E2 + E3 | E3 + E6 | E1 + E3 + E4 | E3 + E5 + E6 | E3 + E4 + E5 + E6 |
| E1 + E4 | E4 + E6 | E2 + E3 + E4 | E1 + E2 + E3 + E6 | E1 + E2 + E3 + E5 |
| E2 + E4 | E5 + E6 | E1 + E2 + E6 | E1 + E2 + E4 + E6 | E1 + E2 + E4 + E5 |
| E3 + E4 | E1 + E2 + E5 | E1 + E3 + E6 | E1 + E2 + E5 + E6 | E1 + E3 + E4 + E5 |
| E1 + E5 | E1 + E3 + E5 | E1 + E4 + E6 | E1 + E3 + E4 + E6 | E2 + E3 + E4 + E5 |
| E2 + E5 | E1 + E4 + E5 | E1 + E5 + E6 | E1 + E3 + E5 + E6 | E1 + E2 + E3 + E4 + E5 |

TABLE E-continued preferred embodiments of the formula (I):

| Combination | Combination | Combination | Combination | Combination |
|---|---|---|---|---|
| E3 + E5 | E2 + E3 + E5 | E2 + E3 + E6 | E1 + E4 + E5 + E6 | E1 + E2 + E3 + E4 + E5 + E6 |
| E4 + E5 | E2 + E4 + E5 | E2 + E4 + E6 | E2 + E3 + E5 + E6 | |

In all of the preferred embodiments mentioned above and the combinations of Table E, $A^1$ is preferably C—$CH_3$, $A^2$ is preferably C—H, $A^3$ is preferably C—H and $A^4$ is preferably C—H.

In a more preferred embodiment of the invention the compounds of the formula (I)

$A^1$ is C—$R^5$, $A^2$, $A^3$ and $A^4$ are C—H;

$R^1$ is hydrogen;

$R^2$ is preferably halogen, amino, $C_1$-$C_4$alkoxy, $C_2$-$C_4$alkenyl, $C_1$-$C_4$haloalkoxy, $C_1$-$C_4$alkylamino, $C_1$-$C_4$dialkylamino, $C_1$-$C_4$haloalkylamino, $C_1$-$C_4$dihaloalkylamino, $C_3$-$C_6$cycloalkyl, $C_1$-$C_4$alkyl substituted by $R^{6a}$ or $C_3$-$C_6$cycloalkyl substituted by $R^{6b}$;

$R^3$ is trifluoromethyl;

$R^4$ is phenyl substituted by one to three $R^7$; especially $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl or 3,4,5-trichloro-phenyl;

$R^5$ is chloro, bromo, trifluoromethyl, ethyl or methyl;

each $R^{6a}$ is independently halogen or cyano;

each $R^{6b}$ is independently halogen, cyano, $C_1$-$C_4$alkyl, $C_1$-$C_4$haloalkyl, $C_1$-$C_4$alkoxy, $C_1$-$C_4$haloalkoxy or $C_1$-$C_4$alkoxy$C_1$-$C_4$alkyl;

each $R^7$ is independently Cl, Br, F or $CF_3$;

In a even more preferred embodiment of the invention the compounds of the formula (I)

$A^1$ is C—$R^5$, $A^2$, $A^3$ and $A^4$ are C—H;

$R^1$ is hydrogen;

$R^2$ is fluoro, cyclopropyl, 1-cyanocyclopropyl, 1-methylcyclopropyl, cyclobutyl, dimethylamino, methylamino, ethylamine, isopropylamino, propylamino, isopropylmethylamino, cyclobutylmethylamino, cyclopropylmethylamino, bis-allylamino, bis-cyclopropylmethylamino, 2-methylpropanenitrile, bis-2,2,2-trifluoroethylamino, bis-2,2-difluoroethylamino methylamino, 2,2,2-trifluoroethylamino, 2,2-difluoroethylamino, 2,2,2-trifluoroethoxy, amino, methyl propanoate, methyl 2,2-dimethylpropanoate or acetonitrile;

$R^3$ is trifluoromethyl;

$R^4$ is phenyl substituted by one to three $R^7$; especially $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3,5-dichloro-4-fluoro-phenyl or 3,4,5-trichloro-phenyl; more especially $R^4$ is 3-chloro-5-trifluoromethyl-phenyl, 3,5-dichloro-phenyl, 3,5-bis-(trifluoromethyl)-phenyl, 3,5-dichloro-4-fluoro-phenyl or 3,4,5-trichloro-phenyl;

$R^5$ is methyl;

each $R^7$ is independently Cl, Br, F or $CF_3$;

The compounds of the invention may be made by a variety of methods as shown in Schemes 1 to 4.

Scheme 1

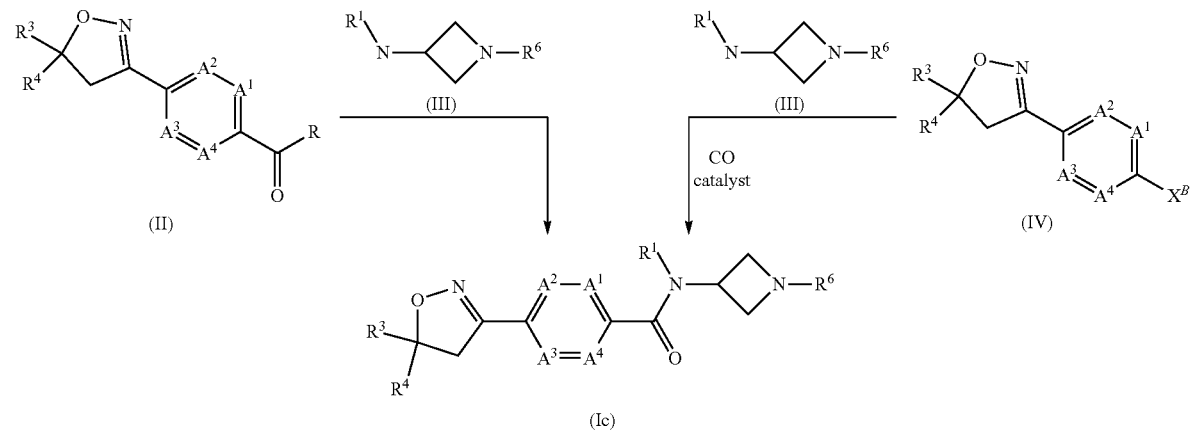

1) Compounds of formula (Ic), wherein $R^6$ is $S(O)_2R^2$, hydrogen or an amine protecting group (usual removable amine protecting groups are described in "Greene's Protective Groups in Organic Synthesis", 4th ed., Wuts, P. G. M., Greene, T. W. 2007, J. Wiley, Hoboken, N.J.), can be prepared by reacting a compound of formula (II) wherein R is OH, $C_1$-$C_6$alkoxy or Cl, F or Br, with an amine of formula (III), as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO 2009/080250.

3) Carboxylic acids of formula (II), wherein R is OH, may be formed from esters of formula (II), wherein R is $C_1$-$C_6$alkoxy as described for example in WO 2009/080250.

4) Compounds of formula (Ic) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropyl-ethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO 2009/080250.

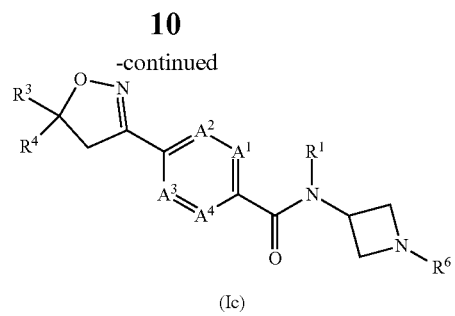
(Ic)

6) Alternatively, compounds of formula (Ic), wherein $R^6$ is $S(O)_2R^2$, hydrogen or an amine protecting group (usual removable amine protecting groups are described in "Greene's Protective Groups in Organic Synthesis", 4th ed., Wuts, P. G. M., Greene, T. W. 2007, J. Wiley, Hoboken, N.J.), can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO 2009/080250. An intermediate of formula (V) can be prepared for example from an intermediate of formula (VI) as described in the same reference.

Scheme 3

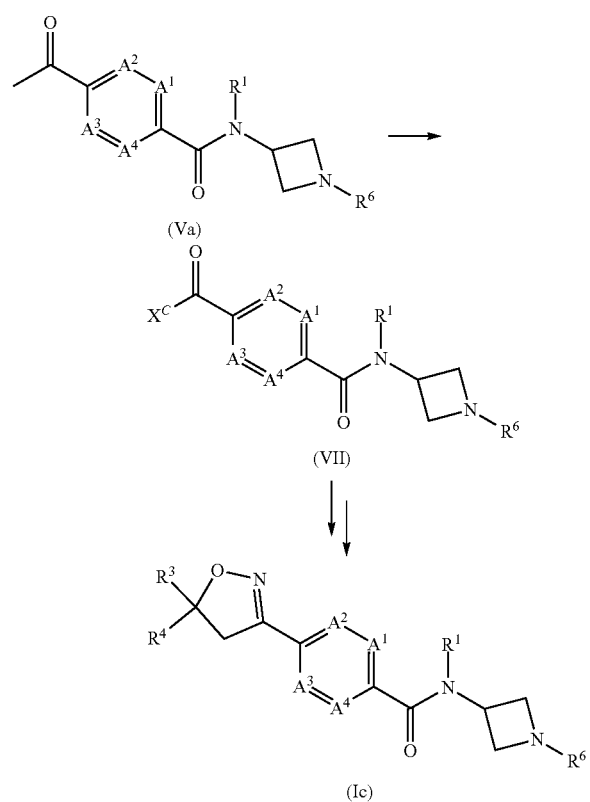

7) Alternatively, compounds of formula (Ic) can be prepared by various methods from an intermediate of formula (VII) as shown in Scheme 3 wherein $X^C$ is CH=C($R^3$)$R^4$, or $CH_2C(OH)(R^3)R^4$ wherein $R^3$ and $R^4$ are as defined for a compound of formula (I) according to similar methods to those described in WO2009080250.

8) Compounds of formula (VII) wherein $X^C$ is CH=C($R^3$)$R^4$, or $CH_2C(OH)(R^3)R^4$ can be prepared from a com- Scheme 2

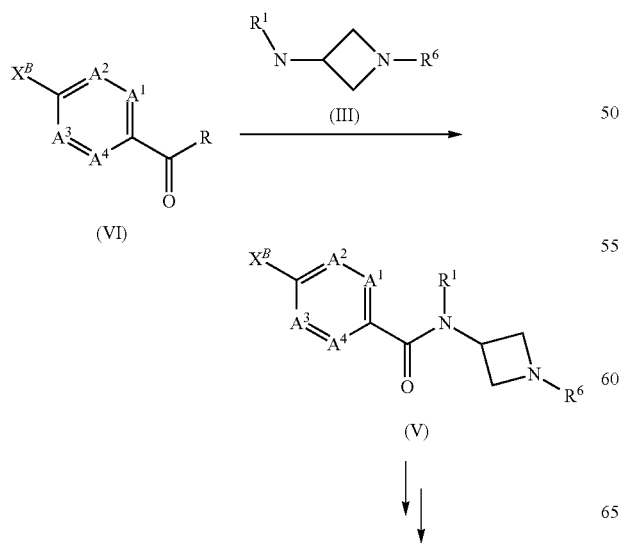

pound of formula (Va) or from a compound of formula (VII) wherein $X^C$ is $CH_2$-halogen using similar methods to those described in WO2009080250.

9) Compounds of formula (VII) wherein $X^C$ is $CH_2$-halogen, such as bromo or chloro, can be prepared by reacting a methyl ketone of formula (Va), with a halogenating agent, such as bromine or chlorine, in a solvent, such as acetic acid, at a temperature of from 0° C. to 50° C., preferably from ambient temperature to 40° C.

Groups in Organic Synthesis", 4th ed., Wuts, P. G. M., Greene, T. W. 2007, J. Wiley, Hoboken, N.J.) as shown in Scheme 4. Such reactions are known to a person skilled in the art.

12) Compounds of formula (Ia) can be prepared by reacting a compound of formula (Id), wherein LG is a suitable leaving group, such as a halogen or an imidazole, with a suitable nucleophile, such as an alcohol, as shown in Scheme 4. Such reactions are usually carried out in the

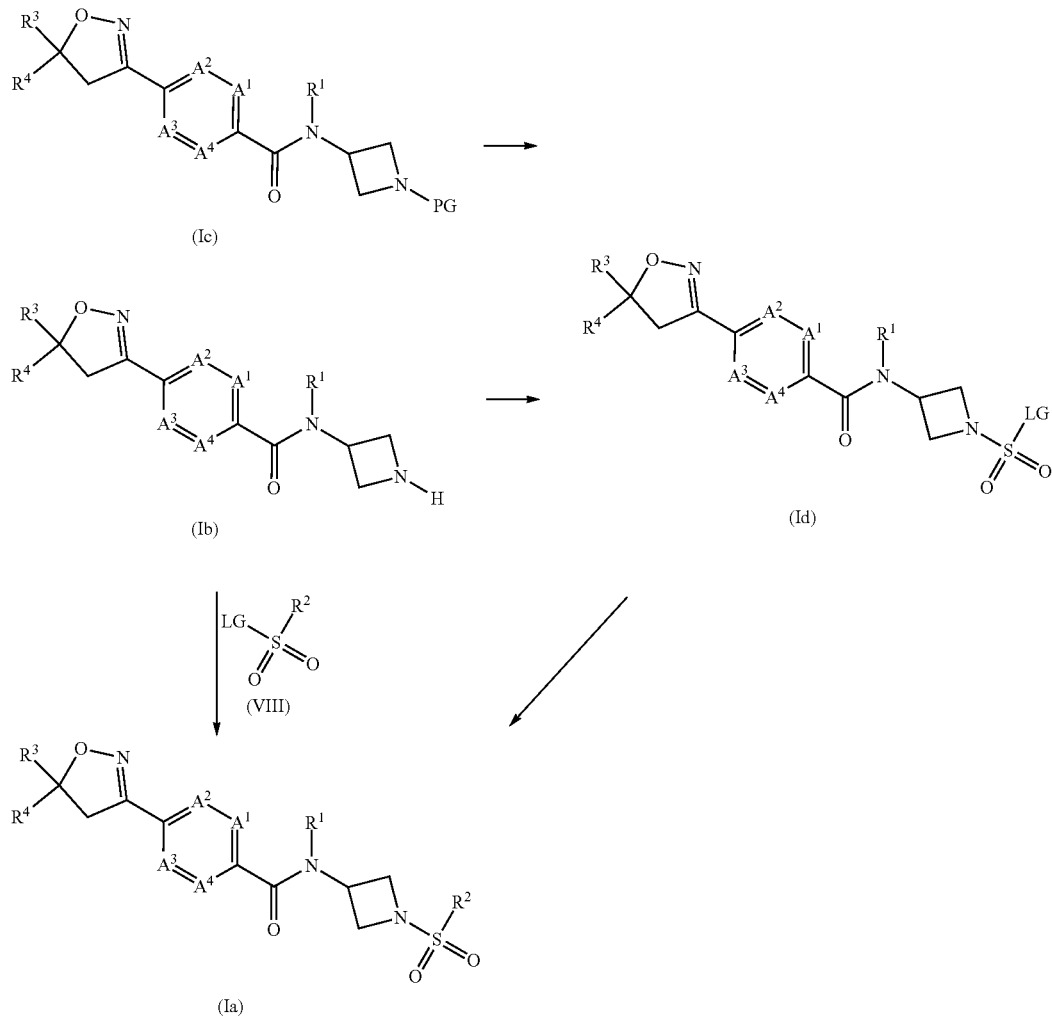

Scheme 4

10) Compounds of formula (Ia) can be prepared by reacting a compound of formula (Ib) with a sulfonyl compound of formula (VIII), wherein LG is a suitable leaving group, such as a halogen atom, such as chlorine, or an imidazole or a substituted phenoxy group, as shown in Scheme 4. Such reactions are usually carried out in the absence or in the presence of a base, such as sodium hydroxide, trimethylamine, sodium hydrogenocarbonate, sodium carbonate, using methods known to a person skilled in the art.

11) In addition, compounds of formula (Ib) can be prepared by deprotecting the amine in a compound of formula (Ic), where PG is an amine protecting group (removable protecting groups are described in "Greene's Protective absence or in the presence of a base, such as sodium hydroxide, trimethylamine, sodium hydrogenocarbonate, sodium carbonate, using methods known to a person skilled in the art.

13) Compounds of formula (Id) can be prepared by reacting a compound of formula (Ib), wherein LG is a suitable leaving group, such as a halogen or an imidazole, with a suitable sulfonyl halide, such as $SO_2F_2$, as shown in Scheme 4. Such reactions are usually carried out in the absence or in the presence of a base, such as sodium hydroxide, trimethylamine, sodium hydrogenocarbonate, sodium carbonate, using methods known to a person skilled in the art.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula (I) can be converted in a manner known per se into another compound of formula (I) by replacing one or more substituents of the starting compound of formula (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

The present invention also provides intermediates useful for the preparation of compounds of formula (I). Certain intermediates are novel and as such form a further aspect of the invention. One group of novel intermediates are compounds of formula (Int-I)

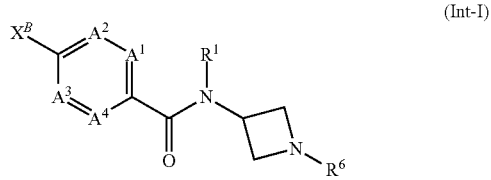

(Int-I)

wherein $A^1$, $A^2$, $A^3$, $A^4$ and $R^1$ are as defined for a compound of formula (I) and $R^6$ is hydrogen or $S(O)_2R^2$ and $X^B$ is a halogen, such as bromo, or $X^B$ is cyano, formyl, CH=N—OH or acetyl; and a salt or N-oxide thereof. The preferences for $A^1$, $A^2$, $A^3$, $A^4$, $R^2$ and $R^1$ are the same as the preferences set out for the corresponding substituents of a compound of formula (I).

Another group of novel intermediates are compounds of formula (Int-II)

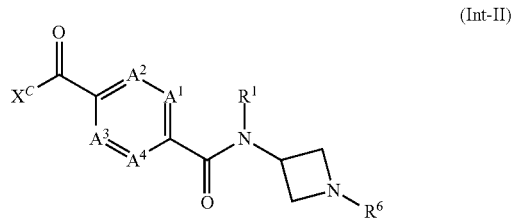

(Int-II)

wherein $A^1$, $A^2$, $A^3$, $A^4$ and $R^1$ are as defined for a compound of formula (I); $R^6$ is hydrogen or $S(O)_2R^2$ and $X^C$ is $CH_2$-halogen, wherein halogen is e.g. bromo or chloro, $CH=C(R^3)R^4$ or $CH_2C(OH)(R^3)R^4$ wherein $R^3$ and $R^4$ are as defined for a compound of formula (I); and a salt or N-oxide thereof. The preferences for $A^1$, $A^2$, $A^3$, $A^4$, $R^2$, $R^3$, $R^4$ and $R^1$ are the same as the preferences set out for the corresponding substituents of a compound of formula (I).

Another group of novel intermediates are compounds of formula (Int-III)

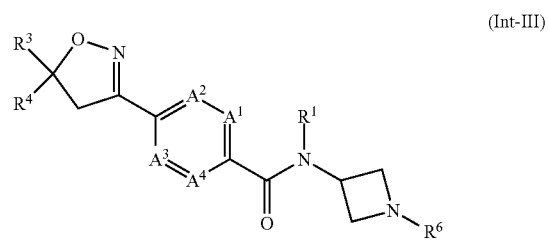

(Int-III)

wherein $A^1$, $A^2$, $A^3$, $A^4$, $R_1$, $R^3$ and $R^4$ are as defined for a compound of formula (I) and $R^6$ is hydrogen or an amine protecting group, such as a boc group (removable protecting groups are described in "Greene's Protective Groups in Organic Synthesis", 4th ed., Wuts, P. G. M., Greene, T. W. 2007, J. Wiley, Hoboken, N.J.) and a salt or N-oxide thereof. The preferences for $A^1$, $A^2$, $A^3$, $A^4$, $R^1$, $R^3$ and $R^4$ are the same as the preferences set out for the corresponding substituents of a compound of formula (I).

The compounds of formula (I) and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents. Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

Compounds of formula (I) include at least one chiral centre and may exist as compounds of formula (I*) or compounds of formula (I**):

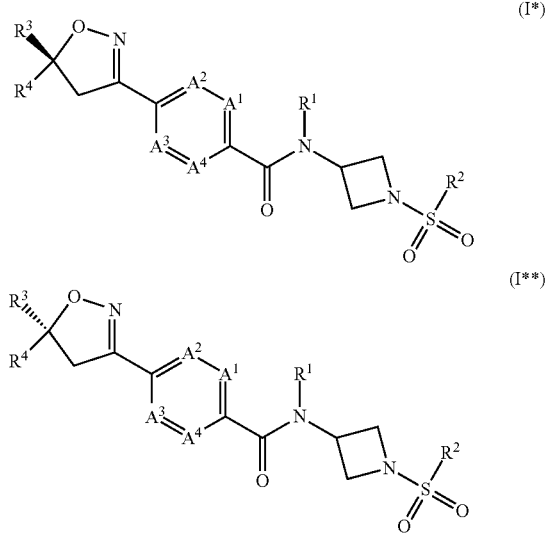

Generally compounds of formula (I**) are more biologically active than compounds of formula (I*). The invention includes mixtures of compounds (I*) and (I) in any ratio e.g. in a molar ratio of 1:99 to 99:1, e.g. 10:1 to 1:10, e.g. a substantially 50:50 molar ratio. In an enantiomerically (or epimerically) enriched mixture of formula (I), the molar proportion of compound (I**) compared to the total amount of both enantiomers (or epimers) is for example greater than 50%, e.g. at least 55, 60, 65, 70, 75, 80, 85, 90, 95, 96, 97, 98, or at least 99%. Likewise, in enantiomerically (or epimerically) enriched mixture of formula (I*), the molar proportion of the compound of formula (I*) compared to the total amount of both enantiomers (or epimers) is for example greater than 50%, e.g. at least 55, 60, 65, 70, 75, 80, 85, 90, 95, 96, 97, 98, or at least 99%. Enantiomerically (or epimerically) enriched mixtures of formula (I**) are preferred.

Salts of compounds of formula (I) can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula (I) can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula (I) can be converted in a manner known per se into other salts of compounds of formula (I), acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula (I), which have salt-forming properties, can be obtained in free form or in the form of salts.

N-oxides can be prepared by reacting a compound of the formula (I) with a suitable oxidizing agent, for example the $H_2O_2$/urea adduct in the presence of an acid anhydride, e.g. trifluoroacetic anhydride.

Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity. The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables A-1 to A-100 below can be prepared according to the methods described above. The examples which follow are intended to illustrate the invention and show preferred compounds of formula (I).

Tables A-1 to A-100: Compounds of Formula (Ia)

The invention is further illustrated by making available the following individual compounds of formula (Ia) listed below in Tables A-1 to A-100.

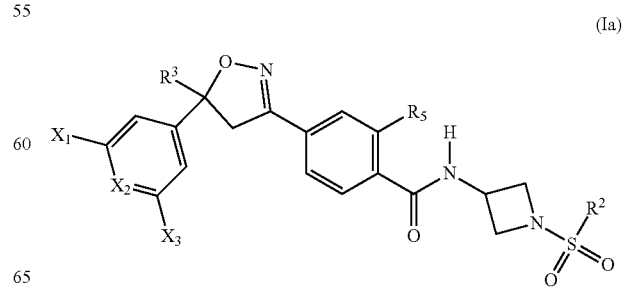

Each of Tables A-1 to A-100, which follow the Table P below, make available compounds of the formula (Ia) in which $X_2$, $R^2$ and $R^3$ are the substituents defined in Table P and $X_1$, $X_3$ and $R^5$ are the substituents defined in the relevant Table A-1 to A-100. Thus Table A-1 individualises compounds of formula (Ia) wherein for each row of Table P, the $X_1$, $X_3$ and $R^5$ substituents are as defined in Table A-1; similarly, Table A-2 individualises compounds of formula (Ia) wherein for each row of Table P, the $X_1$, $X_3$ and $R^5$ substituents are as defined in Table A-2; and so on for Tables A-3 to A-100.

Each compound disclosed in Tables A-1 to A-100 represents a disclosure of a compound according to the compound of formula (I*), and a disclosure according to the compound of formula (I**) as well as mixtures thereof.

TABLE P

Substituent definitions of $X_2$, $R_2$ and $R_3$:

| Index | R2 | R3 | X2 |
|---|---|---|---|
| 1 | cPr | $CF_3$ | N |
| 2 | cPr | $CF_2Cl$ | N |
| 3 | $NHCH_3$ | $CF_3$ | N |
| 4 | $NHCH_3$ | $CF_2Cl$ | N |
| 5 | $N(CH_3)_2$ | $CF_3$ | N |
| 6 | $N(CH_3)_2$ | $CF_2Cl$ | N |
| 7 | F | $CF_3$ | N |
| 8 | F | $CF_2Cl$ | N |
| 9 | $CH_2CN$ | $CF_3$ | N |
| 10 | $CH_2CN$ | $CF_2Cl$ | N |
| 11 | $N(CH_2CF_3)_2$ | $CF_3$ | N |
| 12 | $N(CH_2CF_3)_2$ | $CF_2Cl$ | N |
| 13 | $NHCH_2CF_3$ | $CF_3$ | N |
| 14 | $NHCH_2CF_3$ | $CF_2Cl$ | N |
| 15 | $N(CH_2CHF_2)_2$ | $CF_3$ | N |
| 16 | $N(CH_2CHF_2)_2$ | $CF_2Cl$ | N |
| 17 | $NH_2$ | $CF_3$ | N |
| 18 | $NH_2$ | $CF_2Cl$ | N |
| 19 | cPr | $CF_3$ | C—H |
| 20 | cPr | $CF_2Cl$ | C—H |
| 21 | $NHCH_3$ | $CF_3$ | C—H |
| 22 | $NHCH_3$ | $CF_2Cl$ | C—H |
| 23 | $N(CH_3)_2$ | $CF_3$ | C—H |
| 24 | $N(CH_3)_2$ | $CF_2Cl$ | C—H |
| 25 | F | $CF_3$ | C—H |
| 26 | F | $CF_2Cl$ | C—H |
| 27 | $CH_2CN$ | $CF_3$ | C—H |
| 28 | $CH_2CN$ | $CF_2Cl$ | C—H |
| 29 | $N(CH_2CF_3)_2$ | $CF_3$ | C—H |
| 30 | $N(CH_2CF_3)_2$ | $CF_2Cl$ | C—H |
| 31 | $NHCH_2CF_3$ | $CF_3$ | C—H |
| 32 | $NHCH_2CF_3$ | $CF_2Cl$ | C—H |
| 33 | $N(CH_2CHF_2)_2$ | $CF_3$ | C—H |
| 34 | $N(CH_2CHF_2)_2$ | $CF_2Cl$ | C—H |
| 35 | $NH_2$ | $CF_3$ | C—H |
| 36 | $NH_2$ | $CF_2Cl$ | C—H |
| 37 | cPr | $CF_3$ | C—Cl |
| 38 | cPr | $CF_2Cl$ | C—Cl |
| 39 | $NHCH_3$ | $CF_3$ | C—Cl |
| 40 | $NHCH_3$ | $CF_2Cl$ | C—Cl |
| 41 | $N(CH_3)_2$ | $CF_3$ | C—Cl |
| 42 | $N(CH_3)_2$ | $CF_2Cl$ | C—Cl |
| 43 | F | $CF_3$ | C—Cl |
| 44 | F | $CF_2Cl$ | C—Cl |
| 45 | $CH_2CN$ | $CF_3$ | C—Cl |
| 46 | $CH_2CN$ | $CF_2Cl$ | C—Cl |
| 47 | $N(CH_2CF_3)_2$ | $CF_3$ | C—Cl |
| 48 | $N(CH_2CF_3)_2$ | $CF_2Cl$ | C—Cl |
| 49 | $NHCH_2CF_3$ | $CF_3$ | C—Cl |
| 50 | $NHCH_2CF_3$ | $CF_2Cl$ | C—Cl |
| 51 | $N(CH_2CHF_2)_2$ | $CF_3$ | C—Cl |
| 52 | $N(CH_2CHF_2)_2$ | $CF_2Cl$ | C—Cl |
| 53 | $NH_2$ | $CF_3$ | C—Cl |
| 54 | $NH_2$ | $CF_2Cl$ | C—Cl |
| 55 | cPr | $CF_3$ | C—Br |
| 56 | cPr | $CF_2Cl$ | C—Br |
| 57 | $NHCH_3$ | $CF_3$ | C—Br |
| 58 | $NHCH_3$ | $CF_2Cl$ | C—Br |
| 59 | $N(CH_3)_2$ | $CF_3$ | C—Br |
| 60 | $N(CH_3)_2$ | $CF_2Cl$ | C—Br |
| 61 | F | $CF_3$ | C—Br |
| 62 | F | $CF_2Cl$ | C—Br |
| 63 | $CH_2CN$ | $CF_3$ | C—Br |
| 64 | $CH_2CN$ | $CF_2Cl$ | C—Br |
| 65 | $N(CH_2CF_3)_2$ | $CF_3$ | C—Br |
| 66 | $N(CH_2CF_3)_2$ | $CF_2Cl$ | C—Br |
| 67 | $NHCH_2CF_3$ | $CF_3$ | C—Br |
| 68 | $NHCH_2CF_3$ | $CF_2Cl$ | C—Br |
| 69 | $N(CH_2CHF_2)_2$ | $CF_3$ | C—Br |
| 70 | $N(CH_2CHF_2)_2$ | $CF_2Cl$ | C—Br |
| 71 | $NH_2$ | $CF_3$ | C—Br |
| 72 | $NH_2$ | $CF_2Cl$ | C—Br |
| 73 | cPr | $CF_3$ | C—F |
| 74 | cPr | $CF_2Cl$ | C—F |
| 75 | $NHCH_3$ | $CF_3$ | C—F |
| 76 | $NHCH_3$ | $CF_2Cl$ | C—F |
| 77 | $N(CH_3)_2$ | $CF_3$ | C—F |
| 78 | $N(CH_3)_2$ | $CF_2Cl$ | C—F |
| 79 | F | $CF_3$ | C—F |
| 80 | F | $CF_2Cl$ | C—F |
| 81 | $CH_2CN$ | $CF_3$ | C—F |
| 82 | $CH_2CN$ | $CF_2Cl$ | C—F |
| 83 | $N(CH_2CF_3)_2$ | $CF_3$ | C—F |
| 84 | $N(CH_2CF_3)_2$ | $CF_2Cl$ | C—F |
| 85 | $NHCH_2CF_3$ | $CF_3$ | C—F |
| 86 | $NHCH_2CF_3$ | $CF_2Cl$ | C—F |
| 87 | $N(CH_2CHF_2)_2$ | $CF_3$ | C—F |
| 88 | $N(CH_2CHF_2)_2$ | $CF_2Cl$ | C—F |
| 89 | $NH_2$ | $CF_3$ | C—F |
| 90 | $NH_2$ | $CF_2Cl$ | C—F |
| 91 | cPr | $CF_3$ | C—$CF_3$ |
| 92 | cPr | $CF_2Cl$ | C—$CF_3$ |
| 93 | $NHCH_3$ | $CF_3$ | C—$CF_3$ |
| 94 | $NHCH_3$ | $CF_2Cl$ | C—$CF_3$ |
| 95 | $N(CH_3)_2$ | $CF_3$ | C—$CF_3$ |
| 96 | $N(CH_3)_2$ | $CF_2Cl$ | C—$CF_3$ |
| 97 | F | $CF_3$ | C—$CF_3$ |
| 98 | F | $CF_2Cl$ | C—$CF_3$ |
| 99 | $CH_2CN$ | $CF_3$ | C—$CF_3$ |
| 100 | $CH_2CN$ | $CF_2Cl$ | C—$CF_3$ |
| 101 | $N(CH_2CF_3)_2$ | $CF_3$ | C—$CF_3$ |
| 102 | $N(CH_2CF_3)_2$ | $CF_2Cl$ | C—$CF_3$ |
| 103 | $NHCH_2CF_3$ | $CF_3$ | C—$CF_3$ |
| 104 | $NHCH_2CF_3$ | $CF_2Cl$ | C—$CF_3$ |
| 105 | $N(CH_2CHF_2)_2$ | $CF_3$ | C—$CF_3$ |
| 106 | $N(CH_2CHF_2)_2$ | $CF_2Cl$ | C—$CF_3$ |
| 107 | $NH_2$ | $CF_3$ | C—$CF_3$ |
| 108 | $NH_2$ | $CF_2Cl$ | C—$CF_3$ |
| 109 | $(CH_2)_2CN$ | $CF_3$ | N |
| 110 | $(CH_2)_2CN$ | $CF_2Cl$ | N |
| 111 | $(CH_2)_2CN$ | $CF_3$ | C—H |
| 112 | $(CH_2)_2CN$ | $CF_2Cl$ | C—H |
| 113 | $(CH_2)_2CN$ | $CF_3$ | C—Cl |
| 114 | $(CH_2)_2CN$ | $CF_2Cl$ | C—Cl |
| 115 | $(CH_2)_2CN$ | $CF_3$ | C—Br |
| 116 | $(CH_2)_2CN$ | $CF_2Cl$ | C—Br |
| 117 | $(CH_2)_2CN$ | $CF_3$ | C—F |
| 118 | $(CH_2)_2CN$ | $CF_2Cl$ | C—F |
| 119 | $(CH_2)_2CN$ | $CF_3$ | C—$CF_3$ |
| 120 | $(CH_2)_2CN$ | $CF_2Cl$ | C—$CF_3$ |
| 121 | $C(CH_3)_2CN$ | $CF_3$ | N |
| 122 | $C(CH_3)_2CN$ | $CF_2Cl$ | N |
| 123 | $C(CH_3)_2CN$ | $CF_3$ | C—H |
| 124 | $C(CH_3)_2CN$ | $CF_2Cl$ | C—H |
| 125 | $C(CH_3)_2CN$ | $CF_3$ | C—Cl |
| 126 | $C(CH_3)_2CN$ | $CF_2Cl$ | C—Cl |
| 127 | $C(CH_3)_2CN$ | $CF_3$ | C—Br |
| 128 | $C(CH_3)_2CN$ | $CF_2Cl$ | C—Br |
| 129 | $C(CH_3)_2CN$ | $CF_3$ | C—F |
| 130 | $C(CH_3)_2CN$ | $CF_2Cl$ | C—F |
| 131 | $C(CH_3)_2CN$ | $CF_3$ | C—$CF_3$ |
| 132 | $C(CH_3)_2CN$ | $CF_2Cl$ | C—$CF_3$ |

TABLE P-continued

Substituent definitions of $X_2$, $R_2$ and $R_3$:

| Index | R2 | R3 | X2 |
|---|---|---|---|
| 133 | (CH$_2$)$_2$CH$_3$ | CF$_3$ | N |
| 134 | (CH$_2$)$_2$CH$_3$ | CF$_2$Cl | N |
| 135 | (CH$_2$)$_2$CH$_3$ | CF$_3$ | C—H |
| 136 | (CH$_2$)$_2$CH$_3$ | CF$_2$Cl | C—H |
| 137 | (CH$_2$)$_2$CH$_3$ | CF$_3$ | C—Cl |
| 138 | (CH$_2$)$_2$CH$_3$ | CF$_2$Cl | C—Cl |
| 139 | (CH$_2$)$_2$CH$_3$ | CF$_3$ | C—Br |
| 140 | (CH$_2$)$_2$CH$_3$ | CF$_2$Cl | C—Br |
| 141 | (CH$_2$)$_2$CH$_3$ | CF$_3$ | C—F |
| 142 | (CH$_2$)$_2$CH$_3$ | CF$_2$Cl | C—F |
| 143 | (CH$_2$)$_2$CH$_3$ | CF$_3$ | C—CF$_3$ |
| 144 | (CH$_2$)$_2$CH$_3$ | CF$_2$Cl | C—CF$_3$ |

Table A-1 provides 144 compounds A-1.001 to A-1.144 of formula I(a) wherein $X_1$ is H, $X_3$ is H, $R^5$ is CH$_3$ and $X_2$, $R^2$, $R^3$ are as defined in table P.

Table A-2 provides 144 compounds A-2.001 to A-2.144 of formula I(a) wherein $X_1$ is H, $X_3$ is H, R5 is Cl and $X_2$, $R^2$, $R^3$ are as defined in table P.

Table A-3 provides 144 compounds A-3.001 to A-3.144 of formula I(a) wherein $X_1$ is H, $X_3$ is H, R5 is Br and $X_2$, $R^2$, $R^3$ are as defined in table P.

Table A-4 provides 144 compounds A-4.001 to A-4.144 of formula I(a) wherein $X_1$ is H, $X_3$ is H, R5 is CF$_3$ and $X_2$, $R^2$, $R^3$ are as defined in table P.

Table A-5 provides 144 compounds A-5.001 to A-5.144 of formula I(a) wherein $X_1$ is H, $X_3$ is Cl, R5 is CH$_3$ and $X_2$, $R^2$, $R^3$ are as defined in table P.

Table A-6 provides 144 compounds A-6.001 to A-6.144 of formula I(a) wherein $X_1$ is H, $X_3$ is Cl, R5 is Cl and $X_2$, $R^2$, $R^3$ are as defined in table P.

Table A-7 provides 144 compounds A-7.001 to A-7.144 of formula I(a) wherein $X_1$ is H, $X_3$ is Cl, R5 is Br and $X_2$, $R^2$, $R^3$ are as defined in table P.

Table A-8 provides 144 compounds A-8.001 to A-8.144 of formula I(a) wherein $X_1$ is H, $X_3$ is Cl, R5 is CF$_3$ and $X_2$, $R^2$, $R^3$ are as defined in table P.

Table A-9 provides 144 compounds A-9.001 to A-9.144 of formula I(a) wherein $X_1$ is H, $X_3$ is Br, R5 is CH$_3$ and $X_2$, $R^2$, $R^3$ are as defined in table P.

Table A-10 provides 144 compounds A-10.001 to A-10.144 of formula I(a) wherein $X_1$ is H, $X_3$ is Br, R5 is Cl and $X_2$, $R^2$, $R^3$ are as defined in table P.

Table A-11 provides 144 compounds A-11.001 to A-11.144 of formula I(a) wherein $X_1$ is H, $X_3$ is Br, R5 is Br and $X_2$, $R^2$, $R^3$ are as defined in table P.

Table A-12 provides 144 compounds A-12.001 to A-12.144 of formula I(a) wherein $X_1$ is H, $X_3$ is Br, R5 is CF$_3$ and $X_2$, $R^2$, $R^3$ are as defined in table P.

Table A-13 provides 144 compounds A-13.001 to A-13.144 of formula I(a) wherein $X_1$ is H, $X_3$ is F, R5 is CH$_3$ and $X_2$, $R^2$, $R^3$ are as defined in table P.

Table A-14 provides 144 compounds A-14.001 to A-14.144 of formula I(a) wherein $X_1$ is H, $X_3$ is F, R5 is Cl and $X_2$, $R^2$, $R^3$ are as defined in table P.

Table A-15 provides 144 compounds A-15.001 to A-15.144 of formula I(a) wherein $X_1$ is H, $X_3$ is F, R5 is Br and $X_2$, $R^2$, $R^3$ are as defined in table P.

Table A-16 provides 144 compounds A-16.001 to A-16.144 of formula I(a) wherein $X_1$ is H, $X_3$ is F, R5 is CF$_3$ and $X_2$, $R^2$, $R^3$ are as defined in table P.

Table A-17 provides 144 compounds A-17.001 to A-17.144 of formula I(a) wherein $X_1$ is H, $X_3$ is CF$_3$, R5 is CH$_3$ and $X_2$, $R^2$, $R^3$ are as defined in table P.

Table A-18 provides 144 compounds A-18.001 to A-18.144 of formula I(a) wherein $X_1$ is H, $X_3$ is CF$_3$, R5 is Cl and $X_2$, $R^2$, $R^3$ are as defined in table P.

Table A-19 provides 144 compounds A-19.001 to A-19.144 of formula I(a) wherein $X_1$ is H, $X_3$ is CF$_3$, R5 is Br and $X_2$, $R^2$, $R^3$ are as defined in table P.

Table A-20 provides 144 compounds A-20.001 to A-20.144 of formula I(a) wherein $X_1$ is H, $X_3$ is CF$_3$, R5 is CF$_3$ and $X_2$, $R^2$, $R^3$ are as defined in table P.

Table A-21 provides 144 compounds A-21.001 to A-21.144 of formula I(a) wherein $X_1$ is Cl, $X_3$ is H, R5 is CH$_3$ and $X_2$, $R^2$, $R^3$ are as defined in table P.

Table A-22 provides 144 compounds A-22.001 to A-22.144 of formula I(a) wherein $X_1$ is Cl, $X_3$ is H, R5 is Cl and $X_2$, $R^2$, $R^3$ are as defined in table P.

Table A-23 provides 144 compounds A-23.001 to A-23.144 of formula I(a) wherein $X_1$ is Cl, $X_3$ is H, R5 is Br and $X_2$, $R^2$, $R^3$ are as defined in table P.

Table A-24 provides 144 compounds A-24.001 to A-24.144 of formula I(a) wherein $X_1$ is Cl, $X_3$ is H, R5 is CF$_3$ and $X_2$, $R^2$, $R^3$ are as defined in table P.

Table A-25 provides 144 compounds A-25.001 to A-25.144 of formula I(a) wherein $X_1$ is Cl, $X_3$ is Cl, R5 is CH$_3$ and $X_2$, $R^2$, $R^3$ are as defined in table P.

Table A-26 provides 144 compounds A-26.001 to A-26.144 of formula I(a) wherein $X_1$ is Cl, $X_3$ is Cl, R5 is Cl and $X_2$, $R^2$, $R^3$ are as defined in table P.

Table A-27 provides 144 compounds A-27.001 to A-27.144 of formula I(a) wherein $X_1$ is Cl, $X_3$ is Cl, R5 is Br and $X_2$, $R^2$, $R^3$ are as defined in table P.

Table A-28 provides 144 compounds A-28.001 to A-28.144 of formula I(a) wherein $X_1$ is Cl, $X_3$ is Cl, R5 is CF$_3$ and $X_2$, $R^2$, $R^3$ are as defined in table P.

Table A-29 provides 144 compounds A-29.001 to A-29.144 of formula I(a) wherein $X_1$ is Cl, $X_3$ is Br, R5 is CH$_3$ and $X_2$, $R^2$, $R^3$ are as defined in table P.

Table A-30 provides 144 compounds A-30.001 to A-30.144 of formula I(a) wherein $X_1$ is Cl, $X_3$ is Br, R5 is Cl and $X_2$, $R^2$, $R^3$ are as defined in table P.

Table A-31 provides 144 compounds A-31.001 to A-31.144 of formula I(a) wherein $X_1$ is Cl, $X_3$ is Br, R5 is Br and $X_2$, $R^2$, $R^3$ are as defined in table P.

Table A-32 provides 144 compounds A-32.001 to A-32.144 of formula I(a) wherein $X_1$ is Cl, $X_3$ is Br, R5 is CF$_3$ and $X_2$, $R^2$, $R^3$ are as defined in table P.

Table A-33 provides 144 compounds A-33.001 to A-33.144 of formula I(a) wherein $X_1$ is Cl, $X_3$ is F, R5 is CH$_3$ and $X_2$, $R^2$, $R^3$ are as defined in table P.

Table A-34 provides 144 compounds A-34.001 to A-34.144 of formula I(a) wherein $X_1$ is Cl, $X_3$ is F, R5 is Cl and $X_2$, $R^2$, $R^3$ are as defined in table P.

Table A-35 provides 144 compounds A-35.001 to A-35.144 of formula I(a) wherein $X_1$ is Cl, $X_3$ is F, R5 is Br and $X_2$, $R^2$, $R^3$ are as defined in table P.

Table A-36 provides 144 compounds A-36.001 to A-36.144 of formula I(a) wherein $X_1$ is Cl, $X_3$ is F, R5 is CF$_3$ and $X_2$, $R^2$, $R^3$ are as defined in table P.

Table A-37 provides 144 compounds A-37.001 to A-37.144 of formula I(a) wherein $X_1$ is Cl, $X_3$ is CF$_3$, R5 is CH$_3$ and $X_2$, $R^2$, $R^3$ are as defined in table P.

Table A-38 provides 144 compounds A-38.001 to A-38.144 of formula I(a) wherein $X_1$ is Cl, $X_3$ is CF$_3$, R5 is Cl and $X_2$, $R^2$, $R^3$ are as defined in table P.

Table A-39 provides 144 compounds A-39.001 to A-39.144 of formula I(a) wherein $X_1$ is Cl, $X_3$ is CF$_3$, R5 is Br and $X_2$, $R^2$, $R^3$ are as defined in table P.

Table A-40 provides 144 compounds A-40.001 to A-40.144 of formula I(a) wherein $X_1$ is Cl, $X_3$ is $CF_3$, R5 is $CF_3$ and $X_2$, $R^2$, $R^3$ are as defined in table P.

Table A-41 provides 144 compounds A-41.001 to A-41.144 of formula I(a) wherein $X_1$ is Br, $X_3$ is H, R5 is $CH_3$ and $X_2$, $R^2$, $R^3$ are as defined in table P.

Table A-42 provides 144 compounds A-42.001 to A-42.144 of formula I(a) wherein $X_1$ is Br, $X_3$ is H, R5 is Cl and $X_2$, $R^2$, $R^3$ are as defined in table P.

Table A-43 provides 144 compounds A-43.001 to A-43.144 of formula I(a) wherein $X_1$ is Br, $X_3$ is H, R5 is Br and $X_2$, $R^2$, $R^3$ are as defined in table P.

Table A-44 provides 144 compounds A-44.001 to A-44.144 of formula I(a) wherein $X_1$ is Br, $X_3$ is H, R5 is $CF_3$ and $X_2$, $R^2$, $R^3$ are as defined in table P.

Table A-45 provides 144 compounds A-45.001 to A-45.144 of formula I(a) wherein $X_1$ is Br, $X_3$ is Cl, R5 is $CH_3$ and $X_2$, $R^2$, $R^3$ are as defined in table P.

Table A-46 provides 144 compounds A-46.001 to A-46.144 of formula I(a) wherein $X_1$ is Br, $X_3$ is Cl, R5 is Cl and $X_2$, $R^2$, $R^3$ are as defined in table P.

Table A-47 provides 144 compounds A-47.001 to A-47.144 of formula I(a) wherein $X_1$ is Br, $X_3$ is Cl, R5 is Br and $X_2$, $R^2$, $R^3$ are as defined in table P.

Table A-48 provides 144 compounds A-48.001 to A-48.144 of formula I(a) wherein $X_1$ is Br, $X_3$ is Cl, R5 is $CF_3$ and $X_2$, $R^2$, $R^3$ are as defined in table P.

Table A-49 provides 144 compounds A-49.001 to A-49.144 of formula I(a) wherein $X_1$ is Br, $X_3$ is Br, R5 is $CH_3$ and $X_2$, $R^2$, $R^3$ are as defined in table P.

Table A-50 provides 144 compounds A-50.001 to A-50.144 of formula I(a) wherein $X_1$ is Br, $X_3$ is Br, R5 is Cl and $X_2$, $R^2$, $R^3$ are as defined in table P.

Table A-51 provides 144 compounds A-51.001 to A-51.144 of formula I(a) wherein $X_1$ is Br, $X_3$ is Br, R5 is Br and $X_2$, $R^2$, $R^3$ are as defined in table P.

Table A-52 provides 144 compounds A-52.001 to A-52.144 of formula I(a) wherein $X_1$ is Br, $X_3$ is Br, R5 is $CF_3$ and $X_2$, $R^2$, $R^3$ are as defined in table P.

Table A-53 provides 144 compounds A-53.001 to A-53.144 of formula I(a) wherein $X_1$ is Br, $X_3$ is F, R5 is $CH_3$ and $X_2$, $R^2$, $R^3$ are as defined in table P.

Table A-54 provides 144 compounds A-54.001 to A-54.144 of formula I(a) wherein $X_1$ is Br, $X_3$ is F, R5 is Cl and $X_2$, $R^2$, $R^3$ are as defined in table P.

Table A-55 provides 144 compounds A-55.001 to A-55.144 of formula I(a) wherein $X_1$ is Br, $X_3$ is F, R5 is Br and $X_2$, $R^2$, $R^3$ are as defined in table P.

Table A-56 provides 144 compounds A-56.001 to A-56.144 of formula I(a) wherein $X_1$ is Br, $X_3$ is F, R5 is $CF_3$ and $X_2$, $R^2$, $R^3$ are as defined in table P.

Table A-57 provides 144 compounds A-57.001 to A-57.144 of formula I(a) wherein $X_1$ is Br, $X_3$ is $CF_3$, R5 is $CH_3$ and $X_2$, $R^2$, $R^3$ are as defined in table P.

Table A-58 provides 144 compounds A-58.001 to A-58.144 of formula I(a) wherein $X_1$ is Br, $X_3$ is $CF_3$, R5 is Cl and $X_2$, $R^2$, $R^3$ are as defined in table P.

Table A-59 provides 144 compounds A-59.001 to A-59.144 of formula I(a) wherein $X_1$ is Br, $X_3$ is $CF_3$, R5 is Br and $X_2$, $R^2$, $R^3$ are as defined in table P.

Table A-60 provides 144 compounds A-60.001 to A-60.144 of formula I(a) wherein $X_1$ is Br, $X_3$ is $CF_3$, R5 is $CF_3$ and $X_2$, $R^2$, $R^3$ are as defined in table P.

Table A-61 provides 144 compounds A-61.001 to A-61.144 of formula I(a) wherein $X_1$ is F, $X_3$ is H, R5 is $CH_3$ and $X_2$, $R^2$, $R^3$ are as defined in table P.

Table A-62 provides 144 compounds A-62.001 to A-62.144 of formula I(a) wherein $X_1$ is F, $X_3$ is H, R5 is Cl and $X_2$, $R^2$, $R^3$ are as defined in table P.

Table A-63 provides 144 compounds A-63.001 to A-63.144 of formula I(a) wherein $X_1$ is F, $X_3$ is H, R5 is Br and $X_2$, $R^2$, $R^3$ are as defined in table P.

Table A-64 provides 144 compounds A-64.001 to A-64.144 of formula I(a) wherein $X_1$ is F, $X_3$ is H, R5 is $CF_3$ and $X_2$, $R^2$, $R^3$ are as defined in table P.

Table A-65 provides 144 compounds A-65.001 to A-65.144 of formula I(a) wherein $X_1$ is F, $X_3$ is Cl, R5 is $CH_3$ and $X_2$, $R^2$, $R^3$ are as defined in table P.

Table A-66 provides 144 compounds A-66.001 to A-66.144 of formula I(a) wherein $X_1$ is F, $X_3$ is Cl, R5 is Cl and $X_2$, $R^2$, $R^3$ are as defined in table P.

Table A-67 provides 144 compounds A-67.001 to A-67.144 of formula I(a) wherein $X_1$ is F, $X_3$ is Cl, R5 is Br and $X_2$, $R^2$, $R^3$ are as defined in table P.

Table A-68 provides 144 compounds A-68.001 to A-68.144 of formula I(a) wherein $X_1$ is F, $X_3$ is Cl, R5 is $CF_3$ and $X_2$, $R^2$, $R^3$ are as defined in table P.

Table A-69 provides 144 compounds A-69.001 to A-69.144 of formula I(a) wherein $X_1$ is F, $X_3$ is Br, R5 is $CH_3$ and $X_2$, $R^2$, $R^3$ are as defined in table P.

Table A-70 provides 144 compounds A-70.001 to A-70.144 of formula I(a) wherein $X_1$ is F, $X_3$ is Br, R5 is Cl and $X_2$, $R^2$, $R^3$ are as defined in table P.

Table A-71 provides 144 compounds A-71.001 to A-71.144 of formula I(a) wherein $X_1$ is F, $X_3$ is Br, R5 is Br and $X_2$, $R^2$, $R^3$ are as defined in table P.

Table A-72 provides 144 compounds A-72.001 to A-72.144 of formula I(a) wherein $X_1$ is F, $X_3$ is Br, R5 is $CF_3$ and $X_2$, $R^2$, $R^3$ are as defined in table P.

Table A-73 provides 144 compounds A-73.001 to A-73.144 of formula I(a) wherein $X_1$ is F, $X_3$ is F, R5 is $CH_3$ and $X_2$, $R^2$, $R^3$ are as defined in table P.

Table A-74 provides 144 compounds A-74.001 to A-74.144 of formula I(a) wherein $X_1$ is F, $X_3$ is F, R5 is Cl and $X_2$, $R^2$, $R^3$ are as defined in table P.

Table A-75 provides 144 compounds A-75.001 to A-75.144 of formula I(a) wherein $X_1$ is F, $X_3$ is F, R5 is Br and $X_2$, $R^2$, $R^3$ are as defined in table P.

Table A-76 provides 144 compounds A-76.001 to A-76.144 of formula I(a) wherein $X_1$ is F, $X_3$ is F, R5 is $CF_3$ and $X_2$, $R^2$, $R^3$ are as defined in table P.

Table A-77 provides 144 compounds A-77.001 to A-77.144 of formula I(a) wherein $X_1$ is F, $X_3$ is $CF_3$, R5 is $CH_3$ and $X_2$, $R^2$, $R^3$ are as defined in table P.

Table A-78 provides 144 compounds A-78.001 to A-78.144 of formula I(a) wherein $X_1$ is F, $X_3$ is $CF_3$, R5 is Cl and $X_2$, $R^2$, $R^3$ are as defined in table P.

Table A-79 provides 144 compounds A-79.001 to A-79.144 of formula I(a) wherein $X_1$ is F, $X_3$ is $CF_3$, R5 is Br and $X_2$, $R^2$, $R^3$ are as defined in table P.

Table A-80 provides 144 compounds A-80.001 to A-80.144 of formula I(a) wherein $X_1$ is F, $X_3$ is $CF_3$, R5 is $CF_3$ and $X_2$, $R^2$, $R^3$ are as defined in table P.

Table A-81 provides 144 compounds A-81.001 to A-81.144 of formula I(a) wherein $X_1$ is $CF_3$, $X_3$ is H, R5 is $CH_3$ and $X_2$, $R^2$, $R^3$ are as defined in table P.

Table A-82 provides 144 compounds A-82.001 to A-82.144 of formula I(a) wherein $X_1$ is $CF_3$, $X_3$ is H, R5 is Cl and $X_2$, $R^2$, $R^3$ are as defined in table P.

Table A-83 provides 144 compounds A-83.001 to A-83.144 of formula I(a) wherein $X_1$ is $CF_3$, $X_3$ is H, R5 is Br and $X_2$, $R^2$, $R^3$ are as defined in table P.

Table A-84 provides 144 compounds A-84.001 to A-84.144 of formula I(a) wherein $X_1$ is $CF_3$, $X_3$ is H, R5 is $CF_3$ and $X_2$, $R^2$, $R^3$ are as defined in table P.

Table A-85 provides 144 compounds A-85.001 to A-85.144 of formula I(a) wherein $X_1$ is $CF_3$, $X_3$ is Cl, R5 is $CH_3$ and $X_2$, $R^2$, $R^3$ are as defined in table P.

Table A-86 provides 144 compounds A-86.001 to A-86.144 of formula I(a) wherein $X_1$ is $CF_3$, $X_3$ is Cl, R5 is Cl and $X_2$, $R^2$, $R^3$ are as defined in table P.

Table A-87 provides 144 compounds A-87.001 to A-87.144 of formula I(a) wherein $X_1$ is $CF_3$, $X_3$ is Cl, R5 is Br and $X_2$, $R^2$, $R^3$ are as defined in table P.

Table A-88 provides 144 compounds A-88.001 to A-88.144 of formula I(a) wherein $X_1$ is $CF_3$, $X_3$ is Cl, R5 is $CF_3$ and $X_2$, $R^2$, $R^3$ are as defined in table P.

Table A-89 provides 144 compounds A-89.001 to A-89.144 of formula I(a) wherein $X_1$ is $CF_3$, $X_3$ is Br, R5 is $CH_3$ and $X_2$, $R^2$, $R^3$ are as defined in table P.

Table A-90 provides 144 compounds A-90.001 to A-90.144 of formula I(a) wherein $X_1$ is $CF_3$, $X_3$ is Br, R5 is Cl and $X_2$, $R^2$, $R^3$ are as defined in table P.

Table A-91 provides 144 compounds A-91.001 to A-91.144 of formula I(a) wherein $X_1$ is $CF_3$, $X_3$ is Br, R5 is Br and $X_2$, $R^2$, $R^3$ are as defined in table P.

Table A-92 provides 144 compounds A-92.001 to A-92.144 of formula I(a) wherein $X_1$ is $CF_3$, $X_3$ is Br, R5 is $CF_3$ and $X_2$, $R^2$, $R^3$ are as defined in table P.

Table A-93 provides 144 compounds A-93.001 to A-93.144 of formula I(a) wherein $X_1$ is $CF_3$, $X_3$ is F, R5 is $CH_3$ and $X_2$, $R^2$, $R^3$ are as defined in table P.

Table A-94 provides 144 compounds A-94.001 to A-94.144 of formula I(a) wherein $X_1$ is $CF_3$, $X_3$ is F, R5 is Cl and $X_2$, $R^2$, $R^3$ are as defined in table P.

Table A-95 provides 144 compounds A-95.001 to A-95.144 of formula I(a) wherein $X_1$ is $CF_3$, $X_3$ is F, R5 is Br and $X_2$, $R^2$, $R^3$ are as defined in table P.

Table A-96 provides 144 compounds A-96.001 to A-96.144 of formula I(a) wherein $X_1$ is $CF_3$, $X_3$ is F, R5 is $CF_3$ and $X_2$, $R^2$, $R^3$ are as defined in table P.

Table A-97 provides 144 compounds A-97.001 to A-97.144 of formula I(a) wherein $X_1$ is $CF_3$, $X_3$ is $CF_3$, R5 is $CH_3$ and $X_2$, $R^2$, $R^3$ are as defined in table P.

Table A-98 provides 144 compounds A-98.001 to A-98.144 of formula I(a) wherein $X_1$ is $CF_3$, $X_3$ is $CF_3$, R5 is Cl and $X_2$, $R^2$, $R^3$ are as defined in table P.

Table A-99 provides 144 compounds A-99.001 to A-99.144 of formula I(a) wherein $X_1$ is $CF_3$, $X_3$ is $CF_3$, R5 is Br and $X_2$, $R^2$, $R^3$ are as defined in table P.

Table A-100 provides 144 compounds A-100.001 to A-100.144 of formula I(a) wherein $X_1$ is $CF_3$, $X_3$ is $CF_3$, R5 is $CF_3$ and $X_2$, $R^2$, $R^3$ are as defined in table P.

Examples of compounds of formula (Int-1) made available are those where $X^B$ is bromo, chloro, iodo, cyano, formyl, CH=NOH or acetyl, $A^2$, $A^3$ and $A^4$ are each CH, $R^1$ is hydrogen, $A^1$ is $CR^5$ and $R^6$ is hydrogen or $X^B$ is bromo, chloro, iodo, cyano, formyl, CH=NOH or acetyl, $A^2$, $A^3$ and $A^4$ are each CH, $R^1$ is hydrogen, $A^1$ is $CR^5$ and $R^6$ is $S(O)_2R^2$, wherein $R^2$ and $R^5$ are the substituents defined in Table Q below. Each of Tables B-1 to B-7, which follow the Table Q below, make available compounds of the formula (Int-1) in which $R^2$ and $R^5$ are the substituents defined in Table Q and $X^B$ is as defined in the relevant Table B-1 to B-7.

TABLE Q

| Index | $R^2$ | $R^5$ |
|---|---|---|
| 1 | cPr | $CH_3$ |
| 2 | cPr | Cl |
| 3 | cPr | Br |
| 4 | cPr | $CF_3$ |
| 5 | $NHCH_3$ | $CH_3$ |
| 6 | $NHCH_3$ | Cl |
| 7 | $NHCH_3$ | Br |
| 8 | $NHCH_3$ | $CF_3$ |
| 9 | $N(CH_3)_2$ | $CH_3$ |
| 10 | $N(CH_3)_2$ | Cl |
| 11 | $N(CH_3)_2$ | Br |
| 12 | $N(CH_3)_2$ | $CF_3$ |
| 13 | F | $CH_3$ |
| 14 | F | Cl |
| 15 | F | Br |
| 16 | F | $CF_3$ |
| 17 | $CH_2CN$ | $CH_3$ |
| 18 | $CH_2CN$ | Cl |
| 19 | $CH_2CN$ | Br |
| 20 | $CH_2CN$ | $CF_3$ |
| 21 | $N(CH_2CF_3)_2$ | $CH_3$ |
| 22 | $N(CH_2CF_3)_2$ | Cl |
| 23 | $N(CH_2CF_3)_2$ | Br |
| 24 | $N(CH_2CF_3)_2$ | $CF_3$ |
| 25 | $NHCH_2CF_3$ | $CH_3$ |
| 26 | $NHCH_2CF_3$ | Cl |
| 27 | $NHCH_2CF_3$ | Br |
| 28 | $NHCH_2CF_3$ | $CF_3$ |
| 29 | $N(CH_2CHF_2)_2$ | $CH_3$ |
| 30 | $N(CH_2CHF_2)_2$ | Cl |
| 31 | $N(CH_2CHF_2)_2$ | Br |
| 32 | $N(CH_2CHF_2)_2$ | $CF_3$ |
| 33 | $NH_2$ | $CH_3$ |
| 34 | $NH_2$ | Cl |
| 35 | $NH_2$ | Br |
| 36 | $NH_2$ | $CF_3$ |

Table B-1 provides 36 compounds B-1.01 to B-1.36 of formula (Int-I) wherein $X^B$ is bromo and $R^2$ and $R^5$ are as defined in Table Q.

Table B-2 provides 36 compounds B-2.01 to B-2.36 of formula (Int-I) wherein $X^B$ is chloro and $R^2$ and $R^5$ are as defined in Table Q.

Table B-3 provides 36 compounds B-3.01 to B-3.36 of formula (Int-I) wherein $X^B$ is iodo and $R^2$ and $R^5$ are as defined in Table Q.

Table B-4 provides 36 compounds B-4.01 to B-4.36 of formula (Int-I) wherein $X^B$ is cyano and $R^2$ and $R^5$ are as defined in Table Q.

Table B-5 provides 36 compounds B-5.01 to B-5.36 of formula (Int-I) wherein $X^B$ is formyl and $R^2$ and $R^5$ are as defined in Table Q.

Table B-6 provides 36 compounds B-6.01 to B-6.36 of formula (Int-I) wherein $X^B$ is CH=NOH and $R^2$ and $R^5$ are as defined in Table Q.

Table B-7 provides 36 compounds B-7.01 to B-7.36 of formula (Int-I) wherein $X^B$ is acetyl and $R^2$ and $R^5$ are as defined in Table Q.

Examples of compounds of formula (Int-II) made available are those where $X^C$ is $CH_2Cl$, $CH_2Br$, CH=C($CF_3$)(3-chloro-5-trifluoromethyl-phenyl), CH=C($CF_3$)(3-bromo-5-trifluoromethyl-phenyl), CH=C($CF_3$)(3,5-dichloro-4-fluoro-phenyl), CH=C($CF_3$)(3,4,5-trichloro-phenyl), $CH_2C$(OH)($CF_3$)(3-chloro-5-trifluoromethyl-phenyl), $CH_2C$(OH)($CF_3$)(3-bromo-5-trifluoromethyl-phenyl), $CH_2C$(OH)($CF_3$)(3,5-dichloro-4-fluoro-phenyl) or $CH_2C$(OH)($CF_3$)(3,4,5-trichloro-phenyl), $A^2$, $A^3$ and $A^4$ are each CH, $R^1$ is hydrogen, $A^1$ is $CR^5$ and $R^6$ is hydrogen or $X^C$ is CH2Cl, CH2Br, CH=C($CF_3$)(3-chloro-5-trifluoromethyl-phenyl), CH=C($CF_3$)(3-bromo-5-trifluoromethyl-phenyl), CH=C (CF$_3$)(3,5-dichloro-4-fluoro-phenyl), CH=C(CF$_3$)(3,4,5-trichloro-phenyl), CH$_2$C(OH)(CF$_3$)(3-chloro-5-trifluoromethyl-phenyl), CH$_2$C(OH)(CF$_3$)(3-bromo-5-trifluoromethyl-phenyl), CH$_2$C(OH)(CF$_3$)(3,5-dichloro-4-fluoro-phenyl) or CH$_2$C(OH)(CF$_3$)(3,4,5-trichloro-phenyl), A$^2$, A$^3$ and A$^4$ are each CH, R$^1$ is hydrogen, A$^1$ is CR$^5$ and R$^6$ is S(O)$_2$R$^2$, wherein R$^2$ and R$^5$ correspond to the substitutents R$^2$ and R$^5$ as defined in Table Q above. Each of Tables C-1 to C-10, which follow below, make available compounds of the formula (Int-II) in which R$^2$ and R$^5$ are the substituents defined in Table Q and X$^C$ is as defined in the relevant Table C-1 to C-10.

Table C-1 provides 36 compounds C-1.01 to C-1.36 of formula (Int-II) wherein X$^C$ is CH$_2$Cl and R$^2$ and R$^5$ are as defined in Table Q.

Table C-2 provides 36 compounds C-2.01 to C-2.36 of formula (Int-II) wherein X$^C$ is CH$_2$Br and R$^2$ and R$^5$ are as defined in Table Q.

Table C-3 provides 36 compounds C-3.01 to C-3.36 of formula (Int-II) wherein X$^C$ is CH=C(CF$_3$)(3-chloro-5-trifluoromethyl-phenyl) and R$^2$ and R$^5$ are as defined in Table Q.

Table C-4 provides 36 compounds C-4.01 to C-4.36 of formula (Int-II) wherein X$^C$ is CH=C(CF$_3$)(3-bromo-5-trifluoromethyl-phenyl) and R$^2$ and R$^5$ are as defined in Table Q.

Table C-5 provides 36 compounds C-5.01 to C-5.36 of formula (Int-II) wherein X$^C$ is CH=C(CF$_3$)(3,5-dichloro-4-fluoro-phenyl) and R$^2$ and R$^5$ are as defined in Table Q.

Table C-6 provides 36 compounds C-6.01 to C-6.36 of formula (Int-II) wherein X$^C$ is CH=C(CF$_3$)(3,4,5-trichloro-phenyl) and R$^2$ and R$^5$ are as defined in Table Q.

Table C-7 provides 36 compounds C-7.01 to C-7.36 of formula (Int-II) wherein X$^C$ is CH$_2$C(OH)(CF$_3$)(3-chloro-5-trifluoromethyl-phenyl) and R$^2$ and R$^5$ are as defined in Table Q.

Table C-8 provides 36 compounds C-8.01 to C-8.36 of formula (Int-II) wherein X$^C$ is CH$_2$C(OH)(CF$_3$)(3-bromo-5-trifluoromethyl-phenyl) and R$^2$ and R$^5$ are as defined in Table Q.

Table C-9 provides 36 compounds C-9.01 to C-9.36 of formula (Int-II) wherein X$^C$ is CH$_2$C(OH)(CF$_3$)(3,5-dichloro-4-fluoro-phenyl) and R$^2$ and R$^5$ are as defined in Table Q.

Table C-10 provides 36 compounds C-10.01 to C-10.36 of formula (Int-II) wherein X$^C$ is CH$_2$C(OH)(CF$_3$)(3,4,5-trichloro-phenyl) and R$^2$ and R$^5$ are as defined in Table Q.

The compounds of formula (I) according to the invention are preventively and/or curatively valuable active ingredients in the field of pest control, even at low rates of application, which have a very favorable biocidel spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chori-optes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp., *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*,*Bactrocea pleas*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus conidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hya-

*lopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, *asparagus*, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus* officinalis, Beta vulgarus, Brassica spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusts, V. eriocarpa*) and *Vicia faba*.

Preferred ornamental species include *African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cystforming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; *Citrus* nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); *Opeas; Pomacea* (*P. canaticulata*); *Vallonia* and *Zanitoides*.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example *asparagus*, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula (I).

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Ceram bycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticollis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |

TABLE B-continued

Examples of native woodborers of economic importance.

| Family | Species | Host or Crop Infested |
|---|---|---|
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (*Acarida*) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (*Prostigmata*) and Acaridida (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, takeup enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:

| | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |

Dusts:

| | |
|---|---|
| active ingredient: | 0.1 to 10%, preferably 0.1 to 5% |
| solid carrier: | 99.9 to 90%, preferably 99.9 to 99% |

Suspension Concentrates:

| | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

Wettable Powders:

| | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

Granules:

| | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
|---|---|
| Active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

Coated granules

| | |
|---|---|
| active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula (I) with active ingredients are preferred (the abbreviation "TX" means "one compound selected from the group consisting of the compounds described in Table A-1 to A-100 and A of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fen-pyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+

TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, CDCl3 [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+

TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methyl-rhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DClP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimetho-morph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam 179622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methyl-propyl)-4-[2,2,2-trifluoro-1-methoxy-1-(trifluoromethyl)

ethyl]phenyl]-1H-pyrazole-4-carboxamide [926914-55-8]+TX; lancotrione [1486617-21-3]+TX, florpyrauxifen [943832-81-3]]+TX, ipfentrifluconazole[1417782-08-1]+TX, mefentrifluconazole [1417782-03-6]+TX, quinofumelin [861647-84-9]+TX, chloroprallethrin [399572-87-3]+TX, cyhalodiamide [1262605-53-7]]+TX, fluazaindolizine [1254304-22-7]+TX, fluxametamide [928783-29-3]+TX, epsilon-metofluthrin [240494-71-7]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1]+TX, kappa-tefluthrin [391634-71-2]+TX, fenpicoxamid [517875-34-2]+TX; fluindapyr [1383809-87-7]+TX; alpha-bromadiolone [28772-56-7]+TX; flupyrimin [1689566-03-7]+TX; benzpyrimoxan [1449021-97-9]+TX; acynonapyr [1332838-17-1]+TX; inpyrfluxam [1352994-67-2]+TX, isoflucypram [1255734-28-1]+TX; rescalure [64309-03-1]+TX; aminopyrifen [1531626-08-0]+TX; tyclopyrazoflor [1477919-27-9]+TX; and spiropidion [1229023-00-0]+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ100)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (Bio-Safe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* CrylAb+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmominiatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecaniciffium longisporum* (Vertiblast®)+TX, *Lecaniciffium muscarium* (Vertikil®)+TX, Lymantria Dispar nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®)+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (BioSave®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. Poae (Camperico®)+TX, *Xenorhabdus bovienii*+TX, *Xenorhabdus nematophilus*; and Plant extracts including: pine oil (Retenol®)+TX, azadirachtin (Plasma Neem Oil®)+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botanic®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX, E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline cucumeris®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagrus fusciventris*+TX, *Anagrus kamali*+TX, *Anagrus loecki*+TX, *Anagrus pseudococci* (Citripar®)+

TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (Dac-Digline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys+TX, BioNem H®+TX, Exhibitline Hm®+TX, Larvanem-MC))+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus califomicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-SC))+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus*®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Heroin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (SD-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed. "CAS Reg. No" means the Chemical Abstracts Registry Number.

The active ingredient mixture of the compounds of formula—(I) selected from Table A-1 to A-100 and A with active ingredients described above comprises a compound selected from Table A-1 to A-100 and A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from Table A-1 to A-100 and A and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) selected from Table A-1 to A-100 and A and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula (I). The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

PREPARATORY EXAMPLES

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm, 0.4 ppm, 0.2 ppm, 0.1 ppm or even at lower concentrations.

"Mp" means melting point in ° C. Free radicals represent methyl groups. $^1$H and $^{19}$F NMR measurements were recorded on Brucker 400 MHz or 300 MHz spectrometers, chemical shifts are given in ppm relative to a TMS standard. Spectra measured in deuterated solvents as indicated (br means that the following signal pattern is broad e.g. br s is a broad singlet; s=singlet; d=doublet; m=multiplet).

Example 1 tert-butyl 3-[[4-[(5S)-5-(3,5-dichlorophenyl)-5-(trifluoromethyl)-4H-isoxazol-3-yl]-2-methyl-benzoyl]amino]azetidine-1-carboxylate

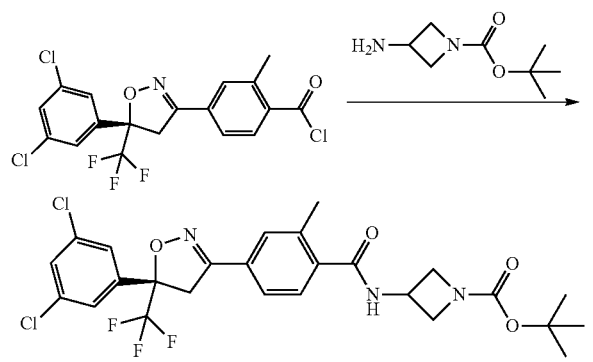

To a cold solution of tert-butyl 3-aminoazetidine-1-carboxylate (440 mg) in dichloromethane (10 mL) was added triethylamine (1 mL) under argon atmosphere. The reaction mixture was stirred for 10 min and then 4-[(5S)-5-(3,5-dichlorophenyl)-5-(trifluoromethyl)-4H-isoxazol-3-yl]-2-methyl-benzoyl chloride (1 g) was slowly added at 0° C. The reaction mixture was stirred for 2.5 h. To the obtained mixture was added an aqueous solution of ammonium chloride (10 mL). The water phase was sepatated and extracted with ethyl acetate. The organic phases were combined, dried over sodium sulfate, filtered and evaporated under reduced pressure. The obtained crude was purified by chromatography over silica gel with ethyl acetate-cyclohexane mixture as an eluent (gradient from 0:1 to 1:1), to give tert-butyl 3-[[4-[(5S)-5-(3,5-dichlorophenyl)-5-(trifluoromethyl)-4H-isoxazol-3-yl]-2-methyl-benzoyl]amino]azetidine-1-carboxylate (807 mg) as foam. 1H NMR (400 MHz, CHLOROFORM-d) δ ppm 1.40-1.48 (m, 9H) 2.48 (s, 3H) 3.71 (d, 1H) 3.83 (dd, 2H) 4.05-4.17 (m, 1H) 4.31-4.40 (m, 2H) 4.74-4.86 (m, 1H) 6.22 (br d, 1H) 7.40-7.47 (m, 2H) 7.49-7.57 (m, 4H). 19F NMR (377 MHz, CHLOROFORM-d) δ ppm −79.51 (s, 3F)

Example 2

N-(azetidin-3-yl)-4-[(5S)-5-(3,5-dichlorophenyl)-5-(trifluoromethyl)-4H-isoxazol-3-yl]-2-methyl-benzamide

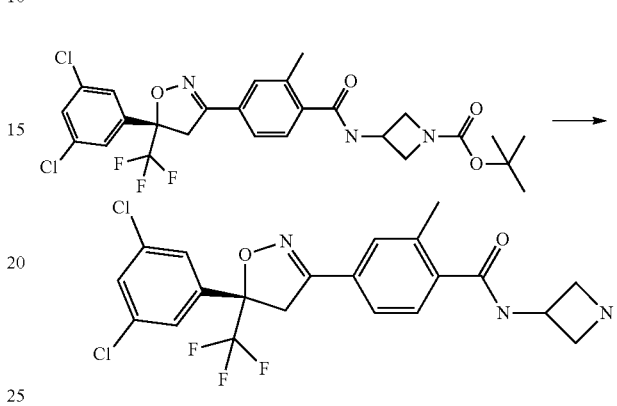

To a solution of tert-butyl 3-[[4-[(5S)-5-(3,5-dichlorophenyl)-5-(trifluoromethyl)-4H-isoxazol-3-yl]-2-methyl-benzoyl]amino]azetidine-1-carboxylate (700 mg) in dichloromethane (4 mL) was added at 0° C. trifluoroacetic acid (947 µl). The resulting solution was stirred at room temperature for 2 h. The reaction mixture was diluted with ethyl acetate-tert-butyl methyl ether (1:1) and poured into a solution of sodium hydroxide (1N). The aqueous phase was extracted with ethyl acetate-tert-butyl methyl ether (1:1). The organic phase was washed with a solution of sodium hydroxide (1N) and then with brine, then combined, dried, filtered and evaporated under reduced pressure to give N-(azetidin-3-yl)-4-[(5S)-5-(3,5-dichlorophenyl)-5-(trifluoromethyl)-4H-isoxazol-3-yl]-2-methyl-benzamide (563 mg) as a foam. 1H NMR (400 MHz, CHLOROFORM-d) δ ppm 2.46 (s, 3H) 3.56 (dd, 2H) 3.70 (d, 1H) 3.99-4.16 (m, 3H) 4.88-5.01 (m, 1H) 6.63 (br d, 1H) 7.38-7.46 (m, 2H) 7.48-7.54 (m, 4H). 19F NMR (377 MHz, CHLOROFORM-d) δ ppm −79.49 (s, 3F)

Example 3

N-(1-cyclopropylsulfonylazetidin-3-yl)-4-[(5S)-5-(3,5-dichlorophenyl)-5-(trifluoromethyl)-4H-isoxazol-3-yl]-2-methyl-benzamide

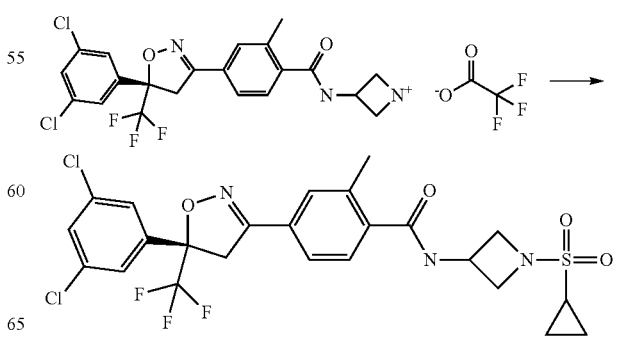

To a cold solution of N-(azetidin-1-ium-3-yl)-4-[(5S)-5-(3,5-dichlorophenyl)-5-(trifluoromethyl)-4H-isoxazol-3-yl]-2-methyl-benzamide; 2,2,2-trifluoroacetate (300 mg) in dichloromethane (3 mL) under argon atmosphere, was added triethylamine (0.14 mL). After stirring for 10 minutes, cyclopropanesulfonyl chloride (76 mg) was added and the reaction mixture was stirred for 1 h. To the obtained mixture was added an aqueous solution of ammonium chloride (10 mL). Then the water phase was separated and extracted with ethyl acetate. The organic phases were combined, dried over magnesium sulfate, filtered and evaporated under reduced pressure. The obtained crude was purified on a preparative UPLC to give N-(1-cyclopropylsulfonylazetidin-3-yl)-4-[(5S)-5-(3,5-dichlorophenyl)-5-(trifluoromethyl)-4H-isoxazol-3-yl]-2-methyl-benzamide (659 mg) as a solid. 1H NMR (400 MHz, CHLOROFORM-d) δ ppm 0.99-1.07 (m, 2H) 1.09-1.19 (m, 2H) 2.34-2.43 (m, 1H) 2.47 (s, 3H) 3.71 (d, 1H) 3.92-4.03 (m, 2H) 4.09 (d, 1H) 4.26 (t, 2H) 4.83-4.96 (m, 1H) 6.37 (br d, 1H) 7.40-7.47 (m, 2H) 7.48-7.59 (m, 4H). 19F NMR (377 MHz, CHLOROFORM-d) δ ppm -79.52 (s, 3F)

Example 4

4-[(5S)-5-(3,5-dichlorophenyl)-5-(trifluoromethyl)-4H-isoxazol-3-yl]-N-[1-(dimethylsulfamoyl)azetidin-3-yl]-2-methyl-benzamide

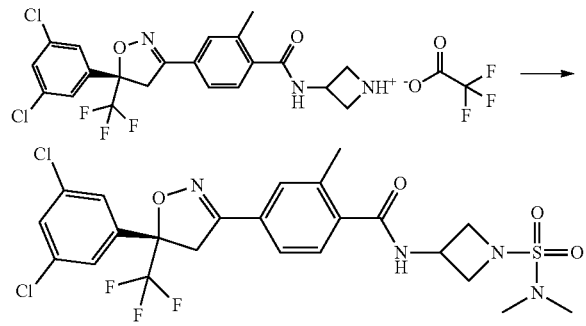

To the solution of N-(azetidin-1-ium-3-yl)-4-[(5S)-5-(3,5-dichlorophenyl)-5-(trifluoromethyl)-4H-isoxazol-3-yl]-2-methyl-benzamide; 2,2,2-trifluoroacetate (300 mg) in dichloromethane (3 mL) under argon atmosphere, was added triethylamine (0.14 mL). After stirring for 10 minutes, to the cold solution was added N,N-dimethylsulfamoyl chloride (80 mg) and the reaction mixtue was stirred for 1 h. To the obtained mixture was added an aqueous solution of ammonium chloride (10 mL). Then the water phase was separated and extracted with ethyl acetate. The organic phases were combined, dried over magnesium sulfate, filtered and evaporated under reduced pressure. The obtained crude was purified by chromatography over silica gel with ethyl acetate-cyclohexane mixture as an eluent (gradient from 0:1 to 0:1), to give 4-[(5S)-5-(3,5-dichlorophenyl)-5-(trifluoromethyl)-4H-isoxazol-3-yl]-N-[1-(dimethylsulfamoyl)azetidin-3-yl]-2-methyl-benzamide (94.1 mg) as a white solid. ¹H NMR (400 MHz, CHLOROFORM-d) δ ppm 2.46 (s, 3H) 2.81 (s, 6H) 3.72 (d, 1H) 3.86-3.95 (m, 2H) 4.09 (d, 1H) 4.14-4.22 (m, 2H) 4.86-4.98 (m, 1H) 6.47 (br d, 1H) 7.39-7.46 (m, 2H) 7.48-7.56 (m, 4H). ¹⁹F NMR (377 MHz, CHLOROFORM-d) δ ppm -79.51 (s, 3F).

Example 5

Preparation of 3-[[4-[(5S)-5-[3-chloro-5-(trifluoromethyl)phenyl]-5-(trifluoromethyl)-4H-isoxazol-3-yl]-2-methyl-benzoyl]amino]azetidine-1-sulfonyl fluoride

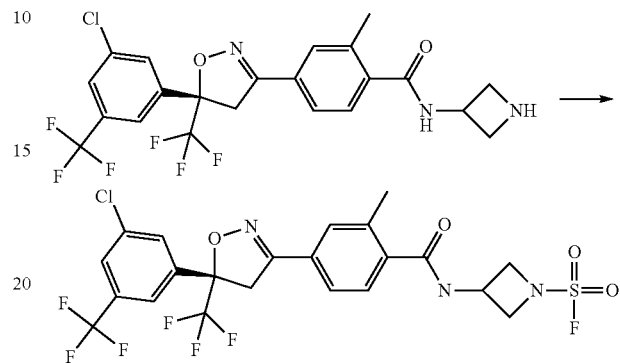

To a solution of N-(azetidin-3-yl)-4-[(5S)-5-[3-chloro-5-(trifluorornethyl)phenyl]-5-(trifluorornethyl)-4H-isoxazol-3-yl]-2-methyl-benzamide (200 mg) in dichloromethane (1.17 mL) was added triethylamine (81.6 mL) followed by sulfuryl fluoride (bubbled in the solution). The reaction mixture was stirred at room temperature for 2 h15. The reaction mixture was then diluted with a mixture of ethyl acetate/tert-butyl methyl ether (ratio 1/1) and poured into a solution of sodium hydroxide (1N). The aqueous phase was extracted with a mixture of ethyl acetate/tert-butyl methyl ether (ratio 1/1). The organic phase was washed with a solution of sodium hydroxide (1N) and then with brine, dried over magnesium sulfate, filtered and evaporated under reduced pressure. The obtained crude was purified by chromatography over silica gel with ethyl acetate-cyclohexane mixture (ratio 4/6) as an eluent to give 3-[[4-[(5S)-5-[3-chloro-5-(trifluoromethyl)phenyl]-5-(trifluoromethyl)-4H-isoxazol-3-yl]-2-methyl-benzoyl]amino]azetidine-1-sulfonyl fluoride (142 mg) as a yellow foam. ¹H NMR (400 MHz, CHLOROFORM-d) δ ppm 2.47 (s, 3H) 3.73 (d, 1H) 4.07-4.20 (m, 3H) 4.48-4.59 (m, 2H) 4.86-5.00 (m, 1H) 6.36 (br d, 1H) 7.43 (d, 1H) 7.49-7.59 (m, 2H) 7.70 (s, 1H) 7.76 (s, 1H) 7.82 (s, 1H).

¹⁹F NMR (377 MHz, CHLOROFORM-d) δ ppm 29.97 (s, 1F), -62.82 (s, 3F), -79.63 (s, 3F).

Example 6

Preparation of 2,2,2-trifluoroethyl 3-[[4-[(5S)-5-[3-chloro-5-(trifluoromethyl)phenyl]-5-(trifluoromethyl)-4H-isoxazol-3-yl]-2-methyl-benzoyl]amino]azetidine-1-sulfonate

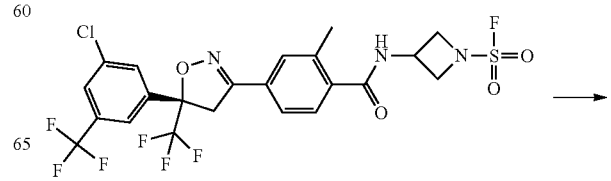

-continued

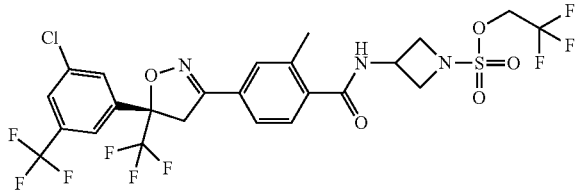

Sodium hydride (5.1 mg) was added to trifluoroethanol (0.510 mL) and stirred for 15 min under an argon atmosphere at room temperature. After 15 minutes, 3-[[4-[(5S)-5-[3-chloro-5-(trifluoromethyl)phenyl]-5-(trifluoromethyl)-4H-isoxazol-3-yl]-2-methyl-benzoyl]amino]azetidine-1-sulfonyl fluoride (50 mg) was added. After 3 h, more sodium hydride (5 mg) was added and the reaction mixture was stirred at room temperature for 18 h. Additional sodium hydride (5 mg) was added and after further 6 h, more sodium hydride (5 mg) was added. After 30 min, additional sodium hydride (10 mg) was added and the reaction mixture was further stirred at room temperature for 18 h. More sodium hydride was added (tip of spatula) and the reaction mixture was further stirred for 24 h. More sodium hydride was added (tip of spatula) and the reaction mixture was further stirred for 7 h30, then more sodium hydride was added (tip of spatula) and the reaction mixture was further stirred for 18 h. The reaction mixture was then quenched with water and extracted with ethyl acetate. The organic phases were washed with water, brine, dried over sodium sulfate, filtered and evaporated under reduced pressure. The obtained crude was purified by column chromatography over silica gel with ethyl acetate-cyclohexane mixture (ratio 3:7) as an eluent to give 2,2,2-trifluoroethyl 3-[[4-[(5S)-5-[3-chloro-5-(trifluoromethyl)phenyl]-5-(trifluoromethyl)-4H-isoxazol-3-yl]-2-methyl-benzoyl]amino]azetidine-1-sulfonate (42 mg) as a colorless oil. $^1$H NMR (400 MHz, CHLOROFORM-d) δ ppm: 2.42 (s, 3H) 3.75 (d, 1H) 4.00-4.18 (m, 3H) 4.39 (t, 2H) 4.48 (q, 2H) 4.84-4.96 (m, 1H) 6.68 (d, 1H) 7.36-7.42 (m, 1H) 7.46-7.53 (m, 2H) 7.70 (s, 1H) 7.76 (s, 1H) 7.82 (s, 1H). $^{19}$F NMR (377 MHz, CHLOROFORM-d) δ ppm: −79.70 (s, 3F) −73.88 (s, 3F) −62.83 (s, 3F).

Example 7

Step 1: Preparation of acetylsulfanylmethyl 2,2-dimethylpropanoate

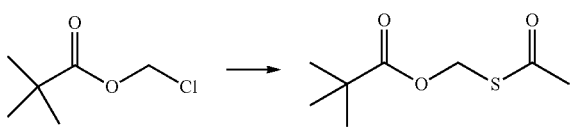

To a solution of chloromethyl pivalate (1 g) in dichloromethane (19 mL) was added at at room temperature diisopropylethylamine (1.73 mL) followed by thioacetic acid (0.538 mL). The reaction mixture was stirred at room temperature for 19 h. The reaction mixture was diluted with ethyl acetate and poured on water. The aqueous phase was extracted with ethyl acetate. The organic phase was washed with water, brine then dried over magnesium sulfate, filtered and evaporated under reduced pressure to give acetylsulfanylmethyl 2,2-dimethylpropanoate (1.51 g) as an oil which was used as such for the next step.

Step 2: Preparation of chlorosulfonylmethyl 2,2-dimethylpropanoate

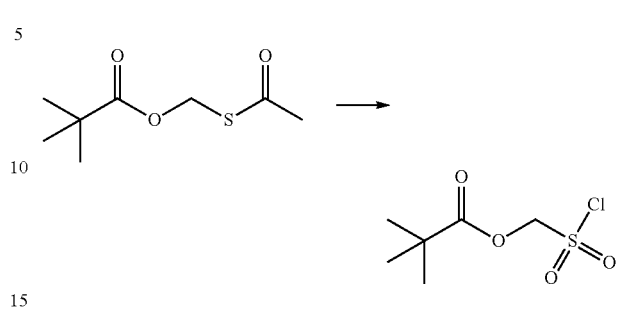

To a suspension of trichloroisocyanuric acid (2.27 g) in acetonitrile (10 mL) at 0° C., was added a 2N aqueous solution of hydrochloric acid (2.68 mL) followed by a solution of acetylsulfanylmethyl 2,2-dimethylpropanoate (1.30 g) in acetonitrile (5.4 mL). The reaction mixture was stirred at 0° C. for 2 h30. The reaction mixture was diluted with ethyl acetate and poured on diethyl ether. The aqueous phase was extracted with diethyl ether. The organic phase was washed with water and brine then dried over magnesium sulfate, filtered and evaporated under reduced pressure to give chlorosulfonylmethyl 2,2-dimethylpropanoate (579 mg) as a colorless oil, which was used without purification for the next step. $^1$H NMR (400 MHz, CHLOROFORM-d) δ ppm 1.24 (s, 9H) 5.72 (s, 2H).

Example 8

Preparation of Chloromethyl Propanoate

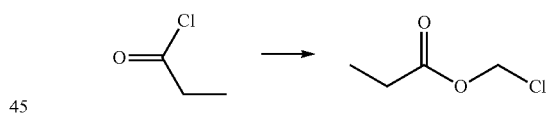

To a mixture of paraformaldehyde (0.479 g) and anhydrous ZnCl$_2$ (41 mg) at −10° C. was added propanoyl chloride (1.35 mL). The reaction mixture was stirred at −10° C. for 1 hour then warmed to room temperature. The suspension was then stirred at room temperature for 15 h. Part of the reaction mixture (500 µL) was diluted with diethyl ether, then poured on aqueous sodium bicarbonate solution (10%). The aqueous phase was extracted with ethyl acetate. The combined organic phases were washed with aqueous sodium bicarbonate solution (10%) and brine then dried over magnesium sulfate, filtered and evaporated under reduced pressure to give chloromethyl propanoate (497 mg) of a colourless oil. The other rest of the reaction mixture was filtered through a pad of silica gel and Celite (w/w 50%) and was washed with petrol ether. The filtrate was evaporated under reduced pressure to give chloromethyl propanoate (387 mg) of a colourless oil.

1H NMR (400 MHz, CHLOROFORM-d) δ ppm 1.18 (t, 3H) 2.42 (q, 2H) 5.71 (s, 2H).

Example 9

Step 1: Preparation of Acetylsulfanylmethyl Propanoate

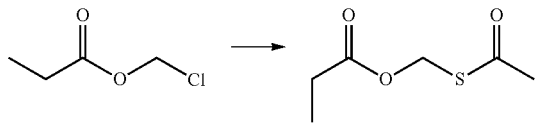

To a solution of chloromethyl propanoate (2.0 g) in ethyl acetate (31 mL) was added triethylamine (2.84 mL) followed by thioacetic acid (1.39 mL). The reaction mixture was stirred at room temperature for 6 h. The reaction mixture was diluted with ethyl acetate and poured on water. The aqueous phase was extracted with ethyl acetate. The combined organic phases were washed with water and brine then dried over magnesium sulfate, filtered and concentrated under reduced pressure to give acetylsulfanylmethyl propanoate (1.99 g) as a yellow oil which was used without further purification. $^1$H NMR (400 MHz, CHLOROFORM-d) δ ppm 1.11-1.16 (m, 3H) 2.32-2.39 (m, 2H) 2.39 (s, 3H) 5.45 (s, 2H).

Step 2: Preparation of Chlorosulfonylmethyl Propanoate

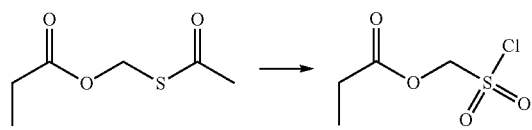

To a suspension of trichloroisocyanuric acid (2.92 g) in acetonitrile (14 mL) at 0° C. was added a 2N aqueous solution of hydrochloric acid (3.45 mL) followed by a solution of acetylsulfanylmethyl propanoate (1.0 g) in acetonitrile (4.5 mL). The reaction mixture was stirred at 0° C. for 1 h15 then it was diluted with diethyl ether and poured on saturated aqueous sodium bicarbonate solution. The aqueous phase was extracted with diethyl ether. The combined organic phases were washed with saturated aqueous sodium bicarbonate solution, brine then dried over magnesium sulfate, filtered and the filtrate was concentrated under reduced pressure to give chlorosulfonylmethyl propanoate (628 mg) as a colourless oil which was used without further purification. $^1$H NMR (400 MHz, CHLOROFORM-d) δ ppm 1.26 (t, 3H) 2.60 (q, 2H) 5.54-5.58 (s, 2H).

Step 3: Preparation of benzyl N-[3-[[4-[(5S)-5-(3,5-dichloro-4-fluoro-phenyl)-5-(trifluoromethyl)-4H-isoxazol-3-yl]-2-methyl-benzoyl]amino]azetidin-1-yl]sulfonylcarbamate

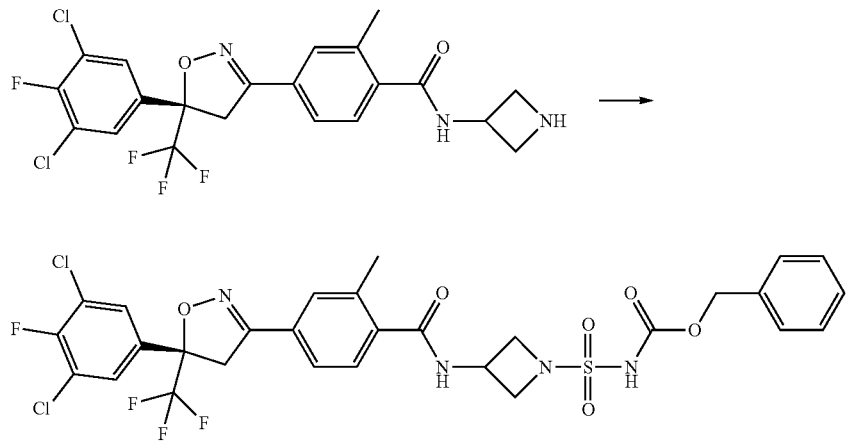

To a solution of N-(azetidin-3-yl)-4-[(5S)-5-(3,5-dichloro-4-fluoro-phenyl)-5-(trifluoromethyl)-4H-isoxazol-3-yl]-2-methyl-benzamide (3.5 g) in ethyl acetate (26 mL) was added trimethylamine (690 mg) followed by a solution of benzyl N-chlorosulfonylcarbamate (1.24 g) and ethyl acetate (10 mL) at −10° C., over 15 minutes. The resulting suspension was stirred at 0° C. for 1.5 hours, then was filtered and the filtrate was concentrated under reduced pressure to give a crude residue, which was purified by chromatography over silica gel with an eluant mixture (toluene/Ethanol/Dioxane/triethylamine/water, in a 5/1/1/1/0.25 ratio) to give benzyl N-[3-[[4-[(5S)-5-(3,5-dichloro-4-fluoro-phenyl)-5-(trifluoromethyl)-4H-isoxazol-3-yl]-2-methyl-benzoyl]amino]azetidin-1-yl]sulfonylcarbamate (2.22 g) as a yellow foam. $^1$H NMR (400 MHz, chloroform-d) δ ppm 2.47 (s, 3H) 3.66 (d, 1H) 3.91-4.01 (m, 2H) 4.02-4.10 (m, 1H) 4.28 (t, 2H) 4.75-4.89 (m, 1H) 4.95 (s, 2H) 7.21-7.26 (m, 5H) 7.39-7.49 (m, 3H) 7.56-7.62 (m, 2H). $^{19}$F NMR (377 MHz, CHLOROFORM-d) δ ppm −113.6 (s, 2F) −79.5 (s, 3F).

Example 10

Preparation of 4-[(5S)-5-(3,5-dichloro-4-fluoro-phenyl)-5-(trifluoromethyl)-4H-isoxazol-3-yl]-2-methyl-N-(1-sulfamoylazetidin-3-yl)benzamide

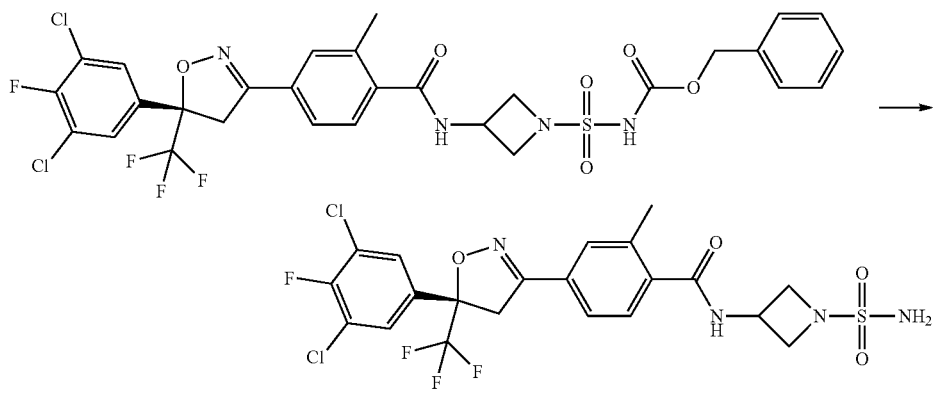

To a solution of benzyl N-[3-[[4-[(5S)-5-(3,5-dichloro-4-fluoro-phenyl)-5-(trifluoromethyl)-4H-isoxazol-3-yl]-2-methyl-benzoyl]amino]azetidin-1-yl]sulfonylcarbamate (2.22 g) in ethanol/THF (9 mL/9 mL) was added at 121 mg of Pd (10% on charcoal) at ambient temperature under argon. The suspension was stirred for 5 minutes then the argon atmosphere was replaced by a hydrogen atmosphere (using a balloon) and the reaction mixture was stirred for 1 h30. The reaction mixture was filtered over a layer of celite and the filtrate was concentrated under reduce pressure to give a crude residue, which was purified by chromatography over silica gel with ethyl acetate-cyclohexane mixture as an eluent (2/1 ratio) to give 4-[(5S)-5-(3,5-dichloro-4-fluoro-phenyl)-5-(trifluoromethyl)-4H-isoxazol-3-yl]-2-methyl-N-(1-sulfamoylazetidin-3-yl)benzamide (1.1 g) as a colorless solid. $^1$H NMR (400 MHz, methanol-d4) δ ppm 2.43 (s, 3H) 3.75-3.84 (m, 2H) 4.02 (d, 1H) 4.07-4.15 (m, 2H) 4.26 (d, 1H) 4.59-4.73 (m, 1H) 7.45 (d, 1H) 7.60-7.66 (m, 2H) 7.74 (d, 2H). $^{19}$F NMR (377 MHz, methanol-d4) δ ppm -116.7 (s, 1F), -81.4 (s, 3F).

Example 11

Preparation of 4-[(5S)-5-(3,5-dichloro-4-fluoro-phenyl)-5-(trifluoromethyl)-4H-isoxazol-3-yl]-2-methyl-N-[1-(2,2,2-trifluoroethylsulfamoyl)azetidin-3-yl]benzamide and N-[1-[bis(2,2,2-trifluoroethyl)sulfamoyl]azetidin-3-yl]-4-[(5S)-5-(3,5-dichloro-4-fluoro-phenyl)-5-(trifluoromethyl)-4H-isoxazol-3-yl]-2-methyl-benzamide

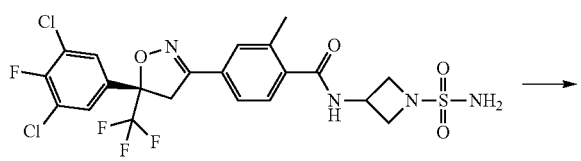

-continued

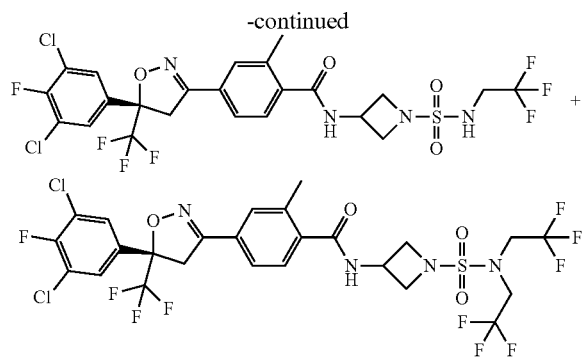

To a solution of 4-[(5S)-5-(3,5-dichloro-4-fluoro-phenyl)-5-(trifluoromethyl)-4H-isoxazol-3-yl]-2-methyl-N-(1-sulfamoylazetidin-3-yl)benzamide (93 mg) in acetonitrile (774 mg) was added cesium carbonate (161 mg) at room temperature, followed by 2,2,2-trifluoroethyl trifluoromethanesulfonate (88 mg). The resulting suspension was stirred at at ambient temperature for 4 hours. It was then diluted with ethyl acetate and poured on water. The aqueous phase was extracted with ethyl acetate. The organic phase was extracted with water and brine then dried over magnesium sulfate and filtered. The filtrate was concentrated under reduced pressure to give a crude residue which was was purified by chromatography over silica gel with ethyl acetate-cyclohexane mixture as an eluent (4/6 ratio) to give N-[1-[bis(2,2,2-trifluoroethyl)sulfamoyl]azetidin-3-yl]-4-[(5S)-5-(3,5-dichloro-4-fluoro-phenyl)-5-(trifluoromethyl)-4H-isoxazol-3-yl]-2-methyl-benzamide and 4-[(5S)-5-(3,5-dichloro-4-fluoro-phenyl)-5-(trifluoromethyl)-4H-isoxazol-3-yl]-2-methyl-N-[1-(2,2,2-trifluoroethylsulfamoyl)azetidin-3-yl]benzamide.

N-[1-[bis(2,2,2-trifluoroethyl)sulfamoyl]azetidin-3-yl]-4-[(5S)-5-(3,5-dichloro-4-fluoro-phenyl)-5-(trifluoromethyl)-4H-isoxazol-3-yl]-2-methyl-benzamide: $^1$H NMR (400 MHz, chloroform-d) δ ppm 2.43 (s, 3H) 3.71 (d, 1H) 3.88-4.09 (m, 7H) 4.25 (t, 2H) 4.82-4.94 (m, 1H) 6.42 (d, 1H) 7.36-7.42 (m, 1H) 7.47-7.52 (m, 2H) 7.59 (d, 2H). $^{19}$F NMR (377 MHz, chloroform-d) δ ppm -113.4 (s, 1F) -79.6 (s, 3F) -69.3 (s, 6F).

4-[(5S)-5-(3,5-dichloro-4-fluoro-phenyl)-5-(trifluoromethyl)-4H-isoxazol-3-yl]-2-methyl-N-[1-(2,2,2-trifluoroethylsulfamoyl)azetidin-3-yl]benzamide: $^1$H NMR (400 MHz, methanol-$d_4$) δ ppm 2.42 (s, 3H) 3.73 (q, 2H) 3.83-3.90 (m, 2H) 4.01 (d, 1H) 4.12 (t, 2H) 4.26 (d, 1H) 4.69 (quin, 1H) 7.43 (d, 1H) 7.57-7.65 (m, 2H) 7.74 (d, 2H). $^{19}$F NMR (377 MHz, methanol-$d_4$) δ ppm −116.6 (s, 1F) −81.4 (s, 3F) −74.4 (s, 6F).

Example 12

Preparation of 7-[5-(3,5-dichloro-4-fluoro-phenyl)-5-(trifluoromethyl)-4H-isoxazol-3-yl]-N-(1-methylsulfonylazetidin-3-yl)indane-4-carboxamide (compound B01)

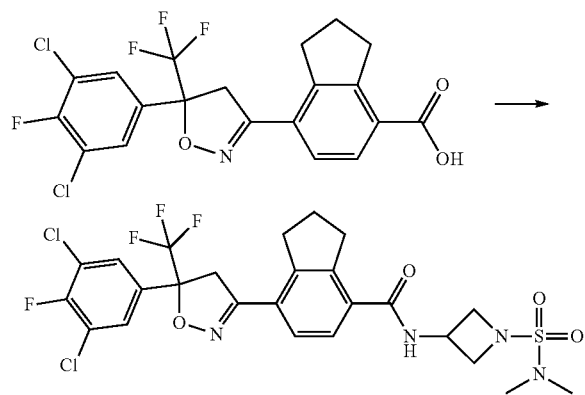

This compound was prepared using a library synthesis approach as described below:

Stock Solutions Preparation:

1-methylsulfonylazetidin-3-amine (0.432 mmol) was dissolved in 2.4 mL of DMA (N,N-dimethylacetamide) to afford the Scaffold stock solutions.

7-[5-(3,5-dichloro-4-fluoro-phenyl)-5-(trifluoromethyl)-4H-isoxazol-3-yl]indane-4-carboxylic acid (0.12 mmol) was dissolved in 0.8 mL of DMA (N,N-dimethylacetamide) to afford the Building Blocks stock solutions.

HATU (502 mg) was dissolved in 16 mL of DMA (N,N-dimethylacetamide) to afford the Coupling agent stock solution.

Dispension and Reaction:

The reactions were carried-out in a 96 well plate. In each well was successively dispensed:

0.2 mL of the Building Block stock solution (0.03 mmol/reaction), 0.2 mL of the Scaffold stock solution (0.036 mmol/reaction), 0.025 mL of diisopropylamine (0.15 mmol/reaction) and 0.4 mL of the Coupling agent stock solution (0.033 mmol/reaction). The well plate was stirred at room temperature overnight then every reaction mixture was mixed with 0.1 ml of methanol before being purified by preparative reverse phase HPLC, to give the desired compound 7-[5-(3,5-dichloro-4-fluoro-phenyl)-5-(trifluoromethyl)-4H-isoxazol-3-yl]-N-(1-methylsulfonylazetidin-3-yl) indane-4-carboxamide (compound B01). UPLC/MS: 2.09 min (retention time), 623.20 (M+H)+ mass measured.

Description of the UPLC Method 1:

Spectra were recorded on a Mass Spectrometer (ACQUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75.

The other compounds were prepared in a similar manner.

TABLE A

Compounds of formula AA (AA)

| Compound number | $A_1$ | $A_2$ | $A_3$ | $A_4$ | $R^2$ |
|---|---|---|---|---|---|
| A01 | Cl | C—F | Cl | $CH_3$ | cPr |
| A02 | Cl | C—F | Cl | $CH_3$ | $N(CH_3)_2$ |
| A03 | Cl | C—H | Cl | $CH_3$ | $N(CH_3)_2$ |
| A04 | Cl | C—H | Cl | $CH_3$ | cPr |
| A05 | Cl | C—F | Cl | $CH_3$ | F |
| A06 | Cl | C—H | Cl | $CH_3$ | F |
| A07 | Cl | C—Cl | Cl | $CH_3$ | F |
| A08 | Cl | C—F | Cl | $CH_3$ | $CH_2CN$ |
| A09 | Cl | C—F | Cl | $CH_3$ | $NHCH_3$ |
| A10 | Cl | C—H | $CF_3$ | $CH_3$ | F |
| A11 | Cl | C—F | Cl | $CH_3$ | 1-methoxymethylcyclopropan-1-yl |
| A12 | Cl | C—F | Cl | $CH_3$ | $NH_2$ |
| A13 | Cl | C—F | Cl | $CH_3$ | $N(CH_2CF_3)_2$ |
| A14 | Cl | C—F | Cl | $CH_3$ | $NHCH_2CF_3$ |
| A15 | Cl | C—H | $CF_3$ | $CH_3$ | $NH_2$ |
| A16 | Cl | C—F | Cl | $CH_3$ | $N(CH_2CHF_2)_2$ |
| A17 | Cl | C—Cl | Cl | $CH_3$ | $CHCH_2$ |
| A18 | Cl | C—H | $CF_3$ | $CH_3$ | $OCH_2CF_3$ |
| A19 | Cl | C—F | Cl | $CH_3$ | $N(CH_2CN)_2$ |
| A20 | Cl | C—F | Cl | $CH_3$ | $NHC(O)N(CH_3)_2$ |
| A21 | Cl | C—F | Cl | $CH_3$ | $C(CH_2)_2CN$ |
| A22 | Cl | C—F | Cl | $CH_3$ | $C(CH_2)_2CH_3$ |
| A23 | Cl | C—F | Cl | $CH_3$ | $C(CH_3)_2CN$ |
| A24 | Cl | C—Cl | Cl | $CH_3$ | $C(CH_2)_2CN$ |
| A25 | Cl | C—Cl | Cl | $CH_3$ | $CH_2OC(O)C(CH_3)_3$ |
| A26 | Cl | C—F | Cl | $CH_3$ | cBu |
| A27 | Cl | C—F | Cl | $CH_3$ | $CH_2OC(O)CH_2CH_3$ |
| A28 | Cl | C—F | Cl | $CH_3$ | $CH_2OC(O)C(CH_3)_3$ |
| B01 | Cl | C—F | Cl | $CH_3$ | $NHCH(CH_3)_2$ |
| B02 | Cl | C—F | Cl | $CH_3$ | $NHCH_2C(O)NH_2$ |
| B03 | Cl | C—F | Cl | $CH_3$ | $NHCH_2CH(CH_3)_2$ |
| B04 | Cl | C—F | Cl | $CH_3$ | $NHCH_2CHC(CH_3)_2$ |
| B05 | Cl | C—F | Cl | $CH_3$ | $NHCH_2CH_3$ |
| B06 | Cl | C—F | Cl | $CH_3$ | $NHCH_2CH_2CH_3$ |
| B07 | Cl | C—F | Cl | $CH_3$ | $NHCH_2CH_2OCH_2CH_2OCH_3$ |
| B08 | Cl | C—F | Cl | $CH_3$ | $N(CH_2CH_2OCH_3)_2$ |
| B09 | Cl | C—F | Cl | $CH_3$ | $N(CH_2C(NOCH_3)CH_3)_2$ |
| B10 | Cl | C—F | Cl | $CH_3$ | $NHCH_2CH_2CN$ |
| B11 | Cl | C—F | Cl | $CH_3$ | $NHCH_2cBu$ |
| B12 | Cl | C—F | Cl | $CH_3$ | $N(allyl)_2$ |
| B13 | Cl | C—F | Cl | $CH_3$ | $NHCH_2CH_2OCH_2CH_3$ |
| B14 | Cl | C—F | Cl | $CH_3$ | $N(CH_2CH_2OCH_2CH_3)_2$ |
| B15 | Cl | C—F | Cl | $CH_3$ | $NHCH_2cPr$ |

TABLE A-continued

Compounds of formula AA (AA)

| Compound number | A₁ | A₂ | A₃ | A₄ | R² |
|---|---|---|---|---|---|
| B16 | Cl | C—F | Cl | CH₃ | N(CH₂cPr)₂ |
| B17 | Cl | C—F | Cl | CH₃ | N(CH₂iPr)₂ |

TABLE A

DATA: NMR data of Compounds of formula AA as described in Table A:

| Compound number | 1H NMR | 19F NMR |
|---|---|---|
| A01 | 1H NMR (400 MHz, CDCl3) δ ppm 1.00-1.21 (m, 4 H) 2.39 (tt, 1 H) 2.48 (s, 3 H) 3.70 (d, 1 H) 3.97 (dd, 2 H) 4.10 (d, 1 H) 4.27 (t, 2 H) 4.86-4.97 (m, 1 H) 6.28 (br d, 1 H) 7.40-7.48 (m, 1 H) 7.50-7.57 (m, 2 H) 7.60 (d, 2 H) | 19F NMR (377 MHz, CDCl3) δ ppm −113.45 (s, 3 F) −79.57 (s, 1 F) |
| A02 | 1H NMR (400 MHz, CDCl3) δ ppm 2.46 (s, 3 H) 2.81 (s, 6 H) 3.71 (d, 1 H) 3.90 (dd, 2 H) 4.04-4.21 (m, 3 H) 4.86-4.98 (m, 1 H) 6.48 (br d, 1 H) 7.39-7.46 (m, 1 H) 7.47-7.55 (m, 2 H) 7.60 (d, 2 H) | 19F NMR (377 MHz, CDCl3) δ ppm −113.47 (s, 1 F) −79.60 (s, 3 F) |
| A03 | 1H NMR (400 MHz, CDCl3) δ ppm 2.46 (s, 3 H) 2.81 (s, 6 H) 3.72 (d, 1 H) 3.90 (dd, 2 H) 4.09 (d, 1 H) 4.14-4.22 (m, 2 H) 4.86-4.97 (m, 1 H) 6.47 (br d, 1 H) 7.40-7.46 (m, 2 H) 7.48-7.55 (m, 4 H) | 19F NMR (377 MHz, CDCl3) δ ppm −79.53 (s, 3 F) |
| A04 | 1H NMR (400 MHz, CDCl3) δ ppm 0.97-1.19 (m, 4 H) 2.33-2.43 (m, 1 H) 2.47 (s, 3 H) 3.71 (d, 1 H) 3.93-4.02 (m, 2 H) 4.09 (d, 1 H) 4.26 (t, 2 H) 4.84-4.97 (m, 1 H) 6.37 (br d, 1 H) 7.39-7.47 (m, 2 H) 7.52 (s, 4 H) | 19F NMR (377 MHz, CDCl3) δ ppm −79.52 (s, 3 F) |
| A05 | 1H NMR (400 MHz, CDCl3) δ ppm 2.49 (s, 3 H) 3.70 (d, 1 H) 4.10 (d, 1 H) 4.13-4.19 (m, 2 H) 4.53-4.60 (m, 2 H) 4.90-5.01 (m, 1 H) 6.24 (br d, 1 H) 7.43-7.48 (m, 1 H) 7.53-7.62 (m, 4 H) | 19F NMR (377 MHz, CDCl3) δ ppm −113.36 (s, 3 F) −79.58 (s, 2 F) 30.02 (s, 1F) |
| A06 | 1H NMR (400 MHz, CDCl3) δ ppm 2.45 (s, 3 H) 3.71 (d, 1 H) 4.04-4.19 (m, 3 H) 4.48-4.58 (m, 2 H) 4.88-5.00 (m, 1 H) 6.51 (d, 1 H) 7.39-7.46 (m, 2 H) 7.48-7.54 (m, 4 H) | 19F NMR (377 MHz, CDCl3) δ ppm −79.55 (s, 3 F) 29.99 (s, 1 F) |
| A07 | 1H NMR (400 MHz, CDCl3) δ ppm 2.45 (s, 3 H) 3.70 (d, 1 H) 4.05-4.18 (m, 3 H) 4.48-4.57 (m, 2 H) 4.88-4.99 (m, 1 H) 6.53 (d, 1 H) 7.38-7.46 (m, 1 H) 7.48-7.55 (m, 2 H) 7.64 (s, 2 H) | 19F NMR (377 MHz, CDCl3) δ ppm −79.47 (s, 3 F) 30.01 (s, 1 F) |
| A08 | 1H NMR (400 MHz, CD3OD) δ ppm 2.43 (s, 3 H) 4.01 (d, 1 H) 4.17-4.31 (m, 3 H) 4.40 (t, 2 H) 4.73-4.82 (m, 1 H) 4.84 (s, 2 H) 7.46 (d, 1 H) 7.58-7.66 (m, 2 H) 7.74 (d, 2 H) | 19F NMR (377 MHz, CD3OD) δ ppm −116.58 (s, 1 F) −81.37 (s, 3 F) |
| A09 | 1H NMR (400 MHz, CDCl3) δ ppm 2.41 (s, 3 H) 2.75 (d, 3 H) 3.66-3.77 (m, 1 H) 3.81-3.92 (m, 2 H) 4.01-4.17 (m, 3 H) 4.29-4.40 (m, 1 H) 4.77-4.91 (m, 1 H) 6.74-6.86 (m, 1 H) 7.32-7.42 (m, 1 H) 7.42-7.50 (m, 2 H) 7.59 (d, 2 H) | 19F NMR (377 MHz, CDCl3) δ ppm −113.47 (s, 1 F) −79.64 (s, 3 F) |
| A10 | 1H NMR (400 MHz, CDCl3) δ ppm 2.47 (s, 3 H) 3.73 (d, 1 H) 4.07-4.20 (m, 3 H) 4.48-4.59 (m, 2 H) 4.86-5.00 (m, 1 H) 6.36 (br d, 1 H) 7.43 (d, 1 H) 7.49-7.59 (m, 2 H) 7.70 (s, 1 H) 7.76 (s, 1 H) 7.82 (s, 1 H) | 19F NMR (377 MHz, CDCl3) δ ppm −79.63 (s, 3 F) −62.82 (s, 3 F) 29.97 (s, 1 F) |
| A11 | 1H NMR (400 MHz, CDCl3) δ ppm 0.98-1.05 (m, 2 H) 1.36-1.45 (m, 2 H) 2.47 (s, 3 H) 3.36 (s, 3 H) 3.62-3.75 (m, 3 H) 3.96 (dd, 2 H) 4.07-4.12 (m, 1 H) 4.33 (t, 2 H) 4.84-4.97 (m, 1 H) 6.48 (d, 1 H) 7.40-7.47 (m, 1 H) 7.50-7.55 (m, 2 H) 7.59 (d, 2 H) | 19F NMR (377 MHz, CDCl3) δ ppm −113.46 (s, 1 F) −79.57 (s, 3 F) |
| A12 | 1H NMR (400 MHz, CD3OD) δ ppm 2.43 (s, 3 H) 3.75-3.84 (m, 2 H) 4.02 (d, 1 H) 4.07-4.15 (m, 2 H) 4.26 (d, 1 H) 4.59-4.73 (m, 1 H) 7.45 (d, 1 H) 7.60-7.66 (m, 2 H) 7.74 (d, 2 H) | 19F NMR (377 MHz, CD3OD) δ ppm −116.69 (s, 1 F) −81.45 (s, 3 F) |
| A13 | 1H NMR (400 MHz, CDCl3) δ ppm 2.43 (s, 3 H) 3.71 (d, 1 H) 3.88-4.09 (m, 7 H) 4.25 (t, 2 H) 4.82-4.94 (m, 1 H) 6.42 (d, 1 H) 7.36-7.42 (m, 1 H) 7.47-7.52 (m, 2 H) 7.59 (d, 2 H) | 19F NMR (377 MHz, CDCl3) δ ppm −113.43 (s, 1 F) −79.65 (s, 3 F) −69.28 (s, 6 F) |
| A14 | 1H NMR (400 MHz, CD3OD) δ ppm 2.42 (s, 3 H) 3.73 (q, 2 H) 3.83-3.90 (m, 2 H) 4.01 (d, 1 H) 4.12 (t, 2 H) 4.26 (d, 1 H) 4.69 (quin, 1 H) 7.43 (d, 1 H) 7.57-7.65 (m, 2 H) 7.74 (d, 2 H) | 19F NMR (377 MHz, CD3OD) δ ppm −116.58 (s, 1 F) −81.39 (s, 3 F) −74.37 (s, 3 F) |
| A15 | 1H NMR (400 MHz, CD3OD) δ ppm 2.43 (s, 3 H) 3.75-3.83 (m, 2 H) 4.00-4.17 (m, 3 H) 4.33 (d, 1 H) 4.63-4.73 (m, 1 H) 7.46 (d, 1 H) 7.60-7.69 (m, 2 H) 7.87 (d, 2 H) 7.96 (s, 1 H) | 19F NMR (377 MHz, CD3OD) δ ppm −81.44 (s, 3 F) −64.35 (s, 3 F) |
| A16 | 1H NMR (400 MHz, CDCl3) δ ppm 2.46 (s, 3 H) 3.60-3.74 (m, 5 H) 3.86-3.93 (m, 2 H) 4.09 (d, 1 H) 4.24 (t, 2 H) 4.83-4.94 (m, 1 H) 5.97 (tt, 2 H) 6.25 (d, 1 H) 7.39-7.45 (m, 1 H) 7.49-7.55 (m, 2 H) 7.59 (d, 2 H) | 19F NMR (377 MHz, CDCl3) δ ppm −121.67 (s, 4 F) −113.43 (s, 1 F) −79.60 (s, 3 F) |
| A17 | 1H NMR (400 MHz, CDCl3) δ ppm 2.46 (s, 3 H) 3.70 (d, 1 H) 3.92 (dd, 2 H) 4.09 (d, 1 H) 4.20 (t, 2 H) 4.78-4.89 (m, 1 H) 6.16 (d, 1 H) 6.32-6.40 (m, 2 H) 6.57 (dd, 1 H) 7.40-7.46 (m, 1 H) 7.49-7.55 (m, 2 H) 7.65 (s, 2 H) | 19F NMR (377 MHz, CDCl3) δ ppm −79.44 (s, 3 F) |
| A18 | 1H NMR (400 MHz, CDCl3) δ ppm 2.42 (s, 3 H) 3.75 (d, 1 H) 4.00-4.18 (m, 3 H) 4.39 (t, 2 H) 4.48 (q, 2 H) 4.84-4.96 (m, 1 H) 6.68 (d, 1 H) 7.36-7.42 (m, 1 H) 7.46-7.53 (m, 2 H) 7.70 (m, 1 H) 7.76 (s, 1 H) 7.82 (s, 1 H) | 19F NMR (377 MHz, CDCl3) δ ppm −79.70 (s, 3 F) −73.88 (s, 3 F) −62.83 (s, 3 F) |
| A19 | 1H NMR (400 MHz, CHLOROFORM-d) δ ppm 2.46 (s, 3 H) 3.71 (d, 1 H) 4.03-4.09 (m, 2 H) 4.27 (s, 4 H) 4.45 (t, 2 1F) | 19F NMR (377 MHz, CHLOROFORM-d) δ ppm −79.57 (s, 3 F), −113.46 (s, 1F) |

TABLE A-continued

DATA: NMR data of Compounds of formula AA as described in Table A:

| | | |
|---|---|---|
| | H) 4.88-4.97 (m, 1 H) 6.56 (d, 1 H) 7.42-7.46 (m, 1 H) 7.49-7.54 (m, 2 H) 7.59 (d, 2 H) | |
| A20 | 1H NMR (400 MHz, DMSO-d6) δ ppm 2.35 (s, 3 H) 2.74-2.95 (m, 6 H) 3.57-3.71 (m, 2 H) 3.79-3.89 (m, 2 H) 4.26-4.43 (m, 3 H) 7.43 (d, 1 H) 7.56-7.60 (m, 2 H) 7.80 (d, 2 H) 8.92 (br d, 1 H) | 19F NMR (377 MHz, DMSO-d6) δ ppm −78.98 (s, 3 F), −115.26 (s, 1F) |
| A21 | 1H NMR (400 MHz, CHLOROFORM-d) δ ppm 1.60-1.80 (m, 4 H) 2.45 (s, 3 H) 3.72 (br d, 1 H) 4.04-4.24 (m, 3 H) 4.48 (t, 2 H) 4.88-5.02 (m, 1 H) 6.57 (br d, 1 H) 7.39-7.47 (m, 1 H) 7.48-7.55 (m, 2 H) 7.59 (d, 2 H) | 19F NMR (377 MHz, CHLOROFORM-d) δ ppm −79.62 (s, 3 F), −113.44 (s, 1F) |
| A22 | 1H NMR (400 MHz, CHLOROFORM-d) δ ppm 0.74-0.79 (m, 2 H) 1.21-1.35 (m, 2 H) 1.50 (s, 3 H) 2.46 (s, 3 H) 3.70 (d, 1 H) 3.92-4.02 (m, 2 H) 4.09 (d, 1 H) 4.20 (t, 2 H) 4.90-5.00 (m, 1 H) 6.44 (d, 1 H) 7.40-7.45 (m, 1 H) 7.49-7.54 (m, 2 H) 7.59 (d, 2 H) | 19F NMR (377 MHz, CHLOROFORM-d) δ ppm −79.60 (s, 3 F), −113.47 (s, 1F) |
| A23 | 1H NMR (400 MHz, CHLOROFORM-d) δ ppm 1.71 (s, 6 H) 2.37 (s, 3 H) 3.74 (d, 1 H) 4.03-4.15 (m, 1 H) 4.22 (ddd, 2 H) 4.37 (t, 2 H) 4.87-5.00 (m, 1 H) 6.91 (d, 1 H) 7.33-7.39 (m, 1 H) 7.39-7.48 (m, 2 H) 7.60 (d, 2 H) | 19F NMR (377 MHz, CHLOROFORM-d) δ ppm −79.70 (s, 3 F), −113.45 (s, 1F) |
| A24 | 1H NMR (400 MHz, CHLOROFORM-d) δ ppm 1.62-1.79 (m, 4 H) 2.46 (s, 3 H) 3.71 (d, 1 H) 4.07-4.21 (m, 3 H) 4.49 (t, 2 H) 4.91-5.00 (m, 1 H) 6.52 (d, 1 H) 7.41-7.46 (m, 1 H) 7.48-7.55 (m, 2 H) 7.65 (s, 2 H) | 19F NMR (377 MHz, CHLOROFORM-d) δ ppm −79.46 (s, 3 F) |
| A25 | 1H NMR (400 MHz, CHLOROFORM-d) δ ppm 1.25(s, 9 H) 2.44 (s, 3 H) 3.72 (d, 1 H) 3.99-4.06 (m, 2 H) 4.10 (d, 1 H) 4.29 (t, 2 H) 4.83-5.01 (m, 1 H) 5.08 (s, 2 H) 6.65 (d, 1 H) 7.39-7.46 (m, 1 H) 7.47-7.54 (m, 2 H) 7.65 (s, 2 H) | 19F NMR (377 MHz, CHLOROFORM-d) δ ppm −79.46 (s, 3 F) |
| A26 | 1H NMR (400 MHz, CHLOROFORM-d) δ ppm 1.93-2.06 (m, 2 H) 2.23-2.34 (m, 2 H) 2.34-2.42 (m, 2 H) 2.44 (s, 3 H) 3.64-3.80 (m, 2 H) 3.97-4.20 (m, 5 H) 4.85-4.99 (m, 1 H) 6.61 (br d, 1 H) 7.38-7.46 (m, 1 H) 7.50 (br d, 2 H) 7.59 (d, 2 H) | 19F NMR (377 MHz, CHLOROFORM-d) δ ppm −79.63 (s, 3 F), −113.46 (s, 1F) |
| A27 | 1H NMR (400 MHz, CHLOROFORM-d) δ ppm 1.17 (t, 3 H) 2.37 (s, 3 H) 2.47 (q, 2 H) 3.74 (d, 1 H) 3.97-4.15 (m, 4 H) 4.26 (t, 2 H) 4.75-4.97 (m, 1 H) 5.04 (s, 1 H) 7.01 (d, 1 H) 7.33-7.39 (m, 1 H) 7.41-7.47 (m, 2 H) 7.59 (d, 2 H) | 19F NMR (377 MHz, CHLOROFORM-d) δ ppm −79.69 (s, 3 F), −113.50 (s, 1F) |
| A28 | 1H NMR (400 MHz, CHLOROFORM-d) δ ppm 1.25 (s, 9 H) 2.38 (s, 3 H) 3.74 (d, 1 H) 3.97-4.16 (m, 3 H) 4.25 (t, 2 H) 4.82-4.99 (m, 1 H) 5.04 (s, 2 H) 6.99 (d, 1 H) 7.34-7.41 (m, 1 H) 7.41-7.47 (m, 2 H) 7.59 (d, 2 H) | 19F NMR (377 MHz, CHLOROFORM-d) δ ppm −79.67 (s, 3 F), −113.50 (s, 1F) |

| Compound number | Retention time (minutes): UPLC/MS method 1 | (M + H) + measured |
|---|---|---|
| B01 | 1.91 | 611.2 |
| B02 | 1.72 | 626.19 |
| B03 | 1.98 | 625.21 |
| B04 | 2 | 637.22 |
| B05 | 1.85 | 597.18 |
| B06 | 1.92 | 611.2 |
| B07 | 1.85 | 671.2 |
| B08 | 1.96 | 685.3 |
| B09 | 2.24 | 739.27 |
| B10 | 1.8 | 622.17 |
| B11 | 2 | 637.22 |
| B12 | 2.1 | 649.2 |
| B13 | 1.89 | 641.22 |
| B14 | 2.1 | 713.3 |
| B15 | 1.93 | 623.2 |
| B16 | 2.17 | 677.3 |
| B17 | 2.28 | 681.31 |

BIOLOGICAL EXAMPLES

These Examples illustrate the pesticidal/insecticidal properties of compounds of formula (Ia).

Tests were performed as follows:

Example B1

*Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:

A01, A02, A03, A04, A05, A06, A07, A08, A09, A10, A11, A12, A13, A14, A15, A16, A17, A18, A19, A20, A21, A22, A23, A24, A25, A26, A27, A28, B01, B02, B03, B04, B05, B06, B07, B08, B10, B11, B12, B13, B14, B15, B16, B17, C01.

Example B2

*Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:

A01, A02, A03, A04, A05, A06, A07, A08, A09, A10, A11, A12, A14, A15, A16, A18, A19, A20, A21, A22, A23, A24, A25, A26, A27, B01, B02, B03, B04, B05, B06, B07, B08, B09, B10, B11, B12, B13, B14, B15, B16, C01.

Example B3

*Myzus persicae* (Green Peach Aphid):Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm:
A01, A02, A03, A05, A06, A07, A09, A10, A11, A12, A13, A14, A15, A19, A21, A22, A23, A24, B01, B02, B05, B06, B07, B08, B10, B12, B15, B16, C01.

Example B4

*Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A01, A02, A03, A04, A05, A06, A07, A08, A09, A10, A11, A12, A13, A14, A15, A16, A17, A18, A19, A20, A21, A22, A23, A24, A25, A26, A27, A28, B01, B02, B03, B04, B05, B06, B07, B08, B09, B10, B11, B12, B13, B14, B15, B16, B17, C01.

Example B5

*Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm:
A01, A02, A03, A04, A05, A06, A07, A08, A09, A10, A11, A12, A13, A14, A15, A16, A17, A18, A19, A20, A21, A22, A23, A24, A25, A26, A27, A28, B01, B02, B03, B04, B05, B06, B07, B08, B09, B10, B11, B12, B13, B14, B15, B16, B17, C01.

Example B6

*Tetranychus urticae* (Two-Spotted Spider Mite):Feeding/Contact Activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A01, A02, A03, A04, A05, A06, A07, A08, A09, A10, A11, A12, A13, A14, A15, A16, A17, A18, A19, A20, A21, A22, A23, A24, A25, A26, A27, A28, B01, B02, B03, B04, B05, B06, B07, B08, B10, B11, B12, B13, B14, B15, B16, C01.

Example B7

*Thrips tabaci* (Onion *Thrips*) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality 6 days after infestation.

The following compounds resulted in at least 80% mortality at an application rate of 200 ppm:
A01, A02, A03, A05, A06, A07, A08, A09, A10, A11, A12, A13, A14, A15, A16, A17, A18, A19, A20, A21, A22, A23, A24, A25, A26, A27, A28, B01, B02, B03, B04, B05, B06, B07, B08, B10, B11, B12, B13, B14, B15, B16, B17, C01.

COMPARATIVE EXAMPLES

Compounds of the invention were tested alongside a number of compounds from WO 2013/026931.

Example C1

*Plutella xylostella* (Diamond Back Moth):Feeding/Contact Activity 24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality (%) 5 days after infestation at the various application rates Example C2

*Spodoptera littoralis* (Egyptian Cotton Leaf Worm):Feeding/Contact Activity

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality (%) 3 days after infestation at the various application rates.

Example C3

*Tetranychus urticae* (Two-Spotted Spider Mite):Feeding/Contact Activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (%) (mobile stages) 8 days after infestation at the various application rates.

Example C4

*Thrips tabaci* (Onion Thrips) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a thrips population of mixed ages. The samples were assessed for mortality (%) 6 days after infestation at the various application rates.

Results of Examples C1 to C4 are shown in Table D below:

TABLE D

| Compound/Test sytem | application rate (ppm) | *Spodoptera littoralis* larval average mortality (%) | *Plutella xylostella* larval average mortality (%) | *Thrips tabaci* mixed population average mortality (%) | *Tetranychus urticae* mixed population average mortality (%) |
|---|---|---|---|---|---|
| WO 2013/026931 Compound A206 | 200 | 100 | 100 | 100 | 100 |
| | 50 | 100 | 100 | 100 | 100 |
| | 12.5 | 100 | 100 | 0 | 100 |
| | 3.12 | 0 | 100 | | 80 |
| | 0.781 | 0 | 80 | | 0 |
| | 0.195 | 0 | 0 | | 0 |
| WO 2013/026931 Compound A205 | 200 | 100 | 100 | 0 | 80 |
| | 50 | 0 | 100 | | 80 |
| | 12.5 | 0 | 100 | 0 | 80 |
| | 3.12 | 0 | 100 | | 50 |
| | 0.781 | 0 | 0 | | 0 |
| | 0.195 | 0 | 0 | | 0 |
| WO 2013/026931 Compound A197 | 200 | 100 | 100 | 90 | 100 |
| | 50 | 100 | 100 | 90 | 100 |
| | 12.5 | 73 | 80 | 0 | 50 |
| | 3.12 | 0 | 0 | | |
| | 0.781 | 0 | 0 | | |
| WO 2013/026931 Compound A196 | 200 | 100 | 100 | 90 | 100 |
| | 50 | 100 | 87 | 80 | 100 |
| | 12.5 | 100 | 80 | 40 | 73 |
| | 3.12 | 0 | 0 | | 0 |
| | 0.781 | 0 | 0 | | 0 |
| WO 2013/026931 Compound A195 | 200 | 100 | 100 | 100 | 100 |
| | 50 | 50 | 100 | 65 | 100 |
| | 12.5 | 0 | 90 | 0 | 58 |
| | 3.12 | | 25 | | 0 |
| | 0.781 | | 0 | | 0 |
| Compound A06 in the application | 200 | 100 | 100 | 100 | 100 |
| | 50 | 100 | 100 | 100 | 100 |
| | 12.5 | 100 | 100 | 100 | 100 |
| | 3.12 | 100 | 100 | 100 | 100 |
| | 0.781 | 100 | 100 | 100 | 100 |
| | 0.195 | 100 | 80 | 0 | 0 |

It can clearly be seen from Table D that the compound of the invention shows improved activity over the compounds from WO 2013/026931 in all of the tests.

What is claimed is:
1. A compound of formula (I),

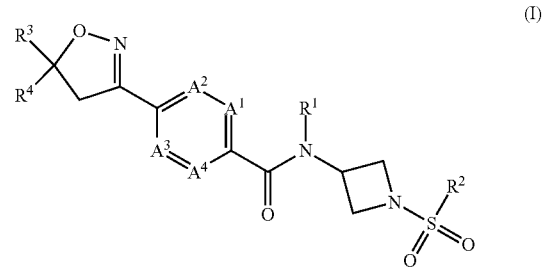

wherein
$A^1$, $A^2$, $A^3$ and $A^4$, independently of one another, are C—H, C—$R^5$ or nitrogen;
$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl;
$R^2$ is halogen, $C_1$-$C_8$alkoxy, amino, $C_2$-$C_6$alkenyl, $C_2$-$C_6$alkynyl, $C_1$-$C_8$haloalkoxy, $C_1$-$C_8$alkylamino, $C_1$-$C_8$alkylamino wherein the alkyl group is substituted by $R^{6a}$, $C_1$-$C_8$alkenylamino, —NHC(O)NR$^a$R$^b$, $C_1$-$C_8$dialkylamino, $C_1$-$C_8$dialkylamino wherein one or both of the alkyl groups are independently substituted by $R^{6a}$, $C_1$-$C_8$dialkenylamino, $C_1$-$C_8$haloalkylamino, $C_1$-$C_8$dihaloalkylamino, $C_3$-$C_8$cycloalkyl, $C_1$-$C_8$alkyl substituted by $R^{6a}$, $C_2$-$C_6$alkenyl substituted by $R^{6b}$, $C_2$-$C_6$alkynyl substituted by $R^{6b}$, $C_3$-$C_8$cycloalkyl substituted by $R^{6b}$ or —R$^c$CO(O)R$^d$, wherein R$^a$ R$^b$, R$^c$ and R$^d$ are independently of each other $C_1$-$C_8$ alkyl;
$R^3$ is $C_1$-$C_8$haloalkyl;
$R^4$ is aryl, aryl substituted by one to three $R^7$, heteroaryl or heteroaryl substituted by one to three $R^7$;
each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH$_2$—CH$_2$—CH$_2$— bridge, a —CH=CH—CH=CH— bridge or a —N=CH—CH=CH— bridge;
each $R^{6a}$ is independently cyano, $C_3$-$C_8$cycloalkyl, $C_2$-$C_8$alkynyl, $C_1$-$C_8$alkoxy, $C_1$-$C_8$alkoxy-$C_1$-$C_8$alkoxy, $C_1$-$C_8$haloalkoxy, $C_1$-$C_8$alkylcarbonyloxy, —C(O)NH$_2$ or =NOR$^f$, wherein R$^f$ is $C_1$-$C_8$ alkyl;
each $R^{6b}$ is independently halogen, cyano, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy or $C_1$-$C_8$alkoxy$C_1$-$C_8$alkyl; and
each $R^7$ is independently halogen, cyano, nitro, $C_1$-$C_8$alkyl, $C_1$-$C_8$haloalkyl, $C_1$-$C_8$alkoxy or $C_1$-$C_8$haloalkoxy;
and agrochemically acceptable salts, stereoisomers, enantiomers, tautomers and N-oxides of those compounds.
2. A compound of formula (I) according to claim 1, wherein
$R^1$ is hydrogen, $C_1$-$C_8$alkyl, $C_1$-$C_8$alkylcarbonyl- or $C_1$-$C_8$alkoxycarbonyl.
3. A compound of formula (I) according to claim 1, wherein
$R^2$ is halogen, $C_1$-$C_4$alkoxy, $C_2$-$C_4$alkenyl, $C_2$-$C_4$alkynyl, $C_1$-$C_4$haloalkoxy, $C_1$-$C_4$alkylamino, $C_1$-$C_4$alkylamino wherein the alkyl group is substituted by $R^{6a}$, $C_1$-$C_4$alkenylamino, —NHC(O)NR$^a$R$^b$, $C_1$-$C_4$dialkylamino, $C_1$-$C_4$dialkylamino wherein one or both of the alkyl groups are independently substituted by $R^{6a}$, $C_1$-$C_4$dialkenylamino, $C_1$-$C_4$haloalkylamino, $C_1$-$C_4$dihaloalkylamino, $C_3$-$C_6$cycloalkyl, $C_1$-$C_4$alkyl substituted by $R^{6a}$, $C_2$-$C_4$alkenyl substituted by $R^{6b}$, $C_2$-$C_4$alkynyl substituted by $R^{6b}$, $C_3$-$C_6$cycloalkyl substituted by $R^{6b}$ or —R$^c$CO(O)R$^d$, wherein R$^a$, R$^b$, R$^a$ and R$^d$ are, independently of each other, $C_1$-$C_8$ alkyl.

4. A compound of formula (I) according to claim 1, wherein
$R^3$ is $C_1$-$C_4$haloalkyl.

5. A compound of formula (I) according to claim 1, wherein
$R^4$ is phenyl or phenyl substituted by one to three $R^7$.

6. A compound of formula (I) according to claim 1, wherein
each $R^5$ is independently halogen, cyano, nitro, $C_1$-$C_8$alkyl, $C_2$-$C_8$ alkenyl, $C_3$-$C_8$cycloalkyl or $C_1$-$C_8$haloalkyl.

7. A compound of formula (I) according to claim 1, wherein
each $R^{6a}$ is independently cyano;
each $R^{6b}$ is independently halogen, cyano, $C_1$-$C_4$alkyl, $C_1$-$C_4$haloalkyl, $C_1$-$C_4$alkoxy, $C_1$-$C_4$haloalkoxy or $C_1$-$C_4$alkoxyC$_1$-$C_4$alkyl.

8. A compound of formula (I) according to claim 1, wherein
each $R^7$ is independently Cl, Br, F or $CF_3$.

9. A compound of formula (I) according to claim 1, wherein
$A^1$ is C—$R^5$ and $A^2$, $A^3$ and $A^4$ are C—H.

10. A pesticidal composition, which comprises a compound of formula (I) according to claim 1 or, where appropriate, a tautomer thereof, in each case in free form or in agrochemically utilizable salt form, as active ingredient and at least one auxiliary.

11. A method for controlling pests, which comprises applying a composition according to claim 10 to the pests or their environment with the exception of a method for treatment of the human or animal body by surgery or therapy and diagnostic methods practiced on the human or animal body.

12. A method for the protection of seeds from the attack by pests, which comprises treating the seeds or the site, where the seeds are planted, with a composition according to claim 10.

13. A compound of formula (I) according to claim 1, wherein $A^1$ is C—$R^5$ and $A^2$, $A^3$ and $A^4$ are C—H.

14. A compound of formula (I) according to claim 13, wherein $R^5$ is methyl.

15. A compound of formula (I) according to claim 14, wherein $R^4$ is phenyl substituted by one to three $R^7$, and each $R^7$ is independently Cl, Br, F or $CF_3$.

16. A compound of formula (I) according to claim 15, wherein $R^1$ is hydrogen.

17. A compound of formula (I) according to claim 15, $R^2$ is halogen, $C_1$-$C_4$alkoxy, $C_2$-$C_4$alkenyl, $C_2$-$C_4$alkynyl, $C_1$-$C_4$haloalkoxy, $C_1$-$C_4$alkylamino, $C_1$-$C_4$alkylamino wherein the alkyl group is substituted by $R^{6a}$, $C_1$-$C_4$alkenylamino, —NHC(O)NR$^a$R$^b$, $C_1$-$C_4$dialkylamino, $C_1$-$C_4$dialkylamino wherein one or both of the alkyl groups are independently substituted by $R^{6a}$, $C_1$-$C_4$dialkylamino, $C_1$-$C_4$haloalkylamino, $C_1$-$C_4$dihaloalkylamino, $C_3$-$C_6$cycloalkyl, $C_1$-$C_4$alkyl substituted by $R^{6a}$, $C_2$-$C_4$alkenyl substituted by $R^{6b}$, $C_2$-$C_4$alkynyl substituted by $R^{6b}$, $C_3$-$C_6$cycloalkyl substituted by $R^{6b}$ or —R$^c$CO(O)R$^d$, wherein R$^a$, R$^b$, R$^c$ and R$^d$ are, independently of each other, $C_1$-$C_8$ alkyl.

18. A compound of formula (Int-I)

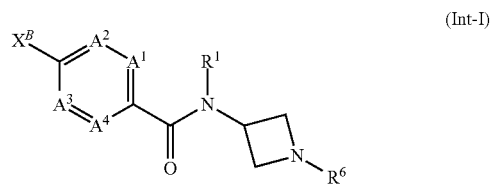

(Int-I)

wherein $A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl;

and $R^6$ is S(O)$_2$R$^2$; and $X^B$ is a halogen, or $X^B$ is cyano, formyl, CH=N—OH or acetyl;

$R^2$ is halogen, $C_1$-$C_8$alkoxy, amino, $C_2$-$C_6$alkenyl, $C_2$-$C_6$alkynyl, $C_1$-$C_8$haloalkoxy, $C_1$-$C_8$alkylamino, $C_1$-$C_8$alkylamino wherein the alkyl group is substituted by $R^{6a}$, $C_1$-$C_8$alkenylamino, —NHC(O)NR$^a$R$^b$, $C_1$-$C_8$dialkylamino, $C_1$-$C_8$dialkylamino wherein one or both of the alkyl groups are independently substituted by $R^{6a}$, $C_1$-$C_8$dialkenylamino, $C_1$-$C_8$haloalkylamino, $C_1$-$C_8$dihaloalkylamino, $C_3$-$C_8$cycloalkyl, $C_1$-$C_8$alkyl substituted by $R^{6a}$, $C_2$-$C_6$alkenyl substituted by $R^{6b}$, $C_2$-$C_6$alkynyl substituted by $R^{6b}$, $C_3$-$C_8$cycloalkyl substituted by $R^{6b}$ or —R$^c$CO(O)R$^d$, wherein R$^a$, R$^b$, R$^c$ and R$^d$ are independently of each other $C_1$-$C_8$ alkyl;

each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —CH$_2$—CH$_2$—CH$_2$— bridge, a —CH=CH—CH=CH— bridge or a —N=CH—CH=CH— bridge;

each $R^{6a}$ is independently cyano, $C_3$-$C_8$cycloalkyl, $C_2$-$C_8$alkynyl, $C_1$-$C_8$alkoxy, $C_1$-$C_8$alkoxy-$C_1$-$C_8$alkoxy, $C_1$-$C_8$haloalkoxy, $C_1$-$C_8$alkylcarbonyloxy, —C(O)NH$_2$ or =NOR$^f$, wherein R$^f$ is $C_1$-$C_8$ alkyl;

each $R^{6b}$ is independently halogen, cyano, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy or $C_1$-$C_8$alkoxyC$_1$-$C_8$alkyl;

$R^3$ is $C_1$-$C_8$haloalkyl;

$R^4$ is aryl, aryl substituted by one to three $R^7$, heteroaryl or heteroaryl substituted by one to three $R^7$;

each $R^7$ is independently halogen, cyano, nitro, $C_1$-$C_8$alkyl, $C_1$-$C_8$haloalkyl, $C_1$-$C_8$alkoxy or $C_1$-$C_8$haloalkoxy; and a salt or N-oxide thereof.

19. A compound of formula (Int-II)

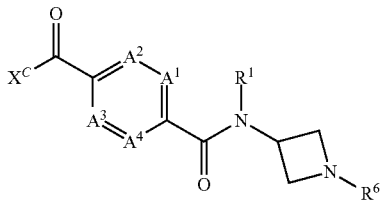

(Int-II)

wherein $A^1$, $A^2$, $A^3$ and $A^4$, independently of one another, are C—H, C—$R^5$ or nitrogen;

$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl or $C_1$-$C_8$alkoxycarbonyl;

$R^6$ is $S(O)_2R^2$;

$X^C$ is $CH_2$-halogen, wherein halogen is bromo or chloro, CH=C($R^3$)$R^4$ or $CH_2C(OH)(R^3)R^4$;

$R^2$ is halogen, $C_1$-$C_8$alkoxy, amino, $C_2$-$C_6$alkenyl, $C_2$-$C_6$alkynyl, $C_1$-$C_8$haloalkoxy, $C_1$-$C_8$alkylamino, $C_1$-$C_8$alkylamino wherein the alkyl group is substituted by $R^{6a}$, $C_1$-$C_8$alkenylamino, —NHC(O)N$R^a R^b$, $C_1$-$C_8$dialkylamino, $C_1$-$C_8$dialkylamino wherein one or both of the alkyl groups are independently substituted by $R^{6a}$, $C_1$-$C_8$dialkenylamino, $C_1$-$C_8$haloalkylamino, $C_1$-$C_8$dihaloalkylamino, $C_3$-$C_8$cycloalkyl, $C_1$-$C_8$alkyl substituted by $R^h$a, $C_2$-$C_6$alkenyl substituted by $R^{6b}$, $C_2$-$C_6$alkynyl substituted by $R^{6b}$, $C_3$-$C_8$cycloalkyl substituted by $R^{6b}$ or —$R^cCO(O)R^d$, wherein $R^a$, $R^b$, $R^c$ and $R^d$ are independently of each other $C_1$-$C_8$ alkyl;

each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, or $C_1$-$C_8$alkoxycarbonyl-, or two $R^5$ on adjacent carbon atoms together form a —$CH_2$—$CH_2$—$CH_2$— bridge, a —CH=CH—CH=CH— bridge or a —N=CH—CH=CH— bridge;

each $R^{6a}$ is independently cyano, $C_3$-$C_8$cycloalkyl, $C_2$-$C_8$alkynyl, $C_1$-$C_8$alkoxy, $C_1$-$C_8$alkoxy-$C_1$-$C_8$alkoxy, $C_1$-$C_8$haloalkoxy, $C_1$-$C_8$alkylcarbonyloxy, —C(O)N$H_2$ or =NO$R^f$, wherein $R^f$ is $C_1$-$C_8$ alkyl;

each $R^{6b}$ is independently halogen, cyano, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy or $C_1$-$C_8$alkoxy$C_1$-$C_8$alkyl;

$R^3$ is $C_1$-$C_8$haloalkyl;

$R^4$ is aryl, aryl substituted by one to three $R^7$, heteroaryl or heteroaryl substituted by one to three $R^7$;

each $R^7$ is independently halogen, cyano, nitro, $C_1$-$C_8$alkyl, $C_1$-$C_8$haloalkyl, $C_1$-$C_8$alkoxy or $C_1$-$C_8$haloalkoxy; and a salt or N-oxide thereof.

20. A compound of formula (Int-III)

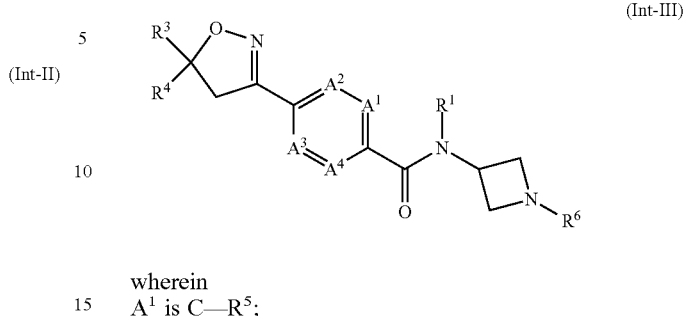

(Int-III)

wherein $A^1$ is C—$R^5$;

$A^2$, $A^3$ and $A^4$, independently are C—H;

$R^1$ is hydrogen;

$R^3$ is $CF_3$;

$R^4$ is phenyl substituted by one to three $R^7$;

$R^5$ is methyl;

$R^6$ is hydrogen;

each $R^7$ is independently halogen or $C_1$ haloalkyl; and a salt or N-oxide thereof.

21. A compound of formula (A4),

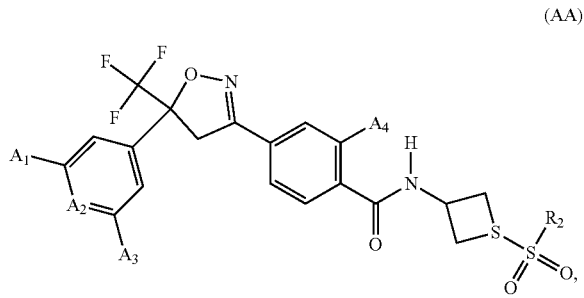

(AA)

wherein $A_1$, $A_2$, $A_3$, $A_4$, and $R^2$ are selected from the following combinations:

| $A_1$ | $A_2$ | $A_3$ | $A_4$ | $R^2$ |
|---|---|---|---|---|
| Cl | C—F | Cl | $CH_3$ | cPr |
| Cl | C—F | Cl | $CH_3$ | $N(CH_3)_2$ |
| Cl | C—H | Cl | $CH_3$ | $N(CH_3)_2$ |
| Cl | C—H | Cl | $CH_3$ | cPr |
| Cl | C—F | Cl | $CH_3$ | F |
| Cl | C—H | Cl | $CH_3$ | F |
| Cl | C—Cl | Cl | $CH_3$ | F |
| Cl | C—F | Cl | $CH_3$ | $CH_2CN$ |
| Cl | C—F | Cl | $CH_3$ | $NHCH_3$ |
| Cl | C—H | $CF_3$ | $CH_3$ | F |
| Cl | C—F | Cl | $CH_3$ | 1-methoxymethylcyclopropan-1-yl |
| Cl | C—F | Cl | $CH_3$ | $NH_2$ |
| Cl | C—F | Cl | $CH_3$ | $N(CH_2CF_3)_2$ |
| Cl | C—F | Cl | $CH_3$ | $NHCH_2CF_3$ |
| Cl | C—H | $CF_3$ | $CH_3$ | $NH_2$ |
| Cl | C—F | Cl | $CH_3$ | $N(CH_2CHF_2)_2$ |
| Cl | C—Cl | Cl | $CH_3$ | $CHCH_2$ |
| Cl | C—H | $CF_3$ | $CH_3$ | $OCH_2CF_3$ |
| Cl | C—F | Cl | $CH_3$ | $N(CH_2CN)_2$ |
| Cl | C—F | Cl | $CH_3$ | $NHC(O)N(CH_3)_2$ |
| Cl | C—F | Cl | $CH_3$ | $C(CH_2)_2CN$ |
| Cl | C—F | Cl | $CH_3$ | $C(CH_2)_2CH_3$ |
| Cl | C—F | Cl | $CH_3$ | $C(CH_3)_2CN$ |
| Cl | C—Cl | Cl | $CH_3$ | $C(CH_2)_2CN$ |
| Cl | C—Cl | Cl | $CH_3$ | $CH_2OC(O)C(CH_3)_3$ |
| Cl | C—F | Cl | $CH_3$ | cBu |

-continued

| $A_1$ | $A_2$ | $A_3$ | $A_4$ | $R^2$ |
|---|---|---|---|---|
| Cl | C—F | Cl | $CH_3$ | $CH_2OC(O)CH_2CH_3$ |
| Cl | C—F | Cl | $CH_3$ | $CH_2OC(O)C(CH_3)_3$ |
| Cl | C—F | Cl | $CH_3$ | $NHCH(CH_3)_2$ |
| Cl | C—F | Cl | $CH_3$ | $NHCH_2C(O)NH_2$ |
| Cl | C—F | Cl | $CH_3$ | $NHCH_2CH(CH_3)_2$ |
| Cl | C—F | Cl | $CH_3$ | $NHCH_2CHC(CH_3)_2$ |
| Cl | C—F | Cl | $CH_3$ | $NHCH_2CH_3$ |
| Cl | C—F | Cl | $CH_3$ | $NHCH_2CH_2CH_3$ |
| Cl | C—F | Cl | $CH_3$ | $NHCH_2CH_2OCH_2CH_2OCH_3$ |
| Cl | C—F | Cl | $CH_3$ | $N(CH_2CH_2OCH_3)_2$ |
| Cl | C—F | Cl | $CH_3$ | $N(CH_2C(NOCH_3)CH_3)_2$ |
| Cl | C—F | Cl | $CH_3$ | $NHCH_2CH_2CN$ |
| Cl | C—F | Cl | $CH_3$ | $NHCH_2cBu$ |
| Cl | C—F | Cl | $CH_3$ | $N(allyl)_2$ |
| Cl | C—F | Cl | $CH_3$ | $NHCH_2CH_2OCH_2CH_3$ |
| Cl | C—F | Cl | $CH_3$ | $N(CH_2CH_2OCH_2CH_3)_2$ |
| Cl | C—F | Cl | $CH_3$ | $NHCH_2cPr$ |
| Cl | C—F | Cl | $CH_3$ | $N(CH_2cPr)_2$ |
| Cl | C—F | Cl | $CH_3$ | $N(CH_2iPr)_2.$ |

\* \* \* \* \*